US008078407B1

(12) United States Patent
Brown

(10) Patent No.: US 8,078,407 B1
(45) Date of Patent: Dec. 13, 2011

(54) SYSTEM AND METHOD FOR IDENTIFYING DISEASE-INFLUENCING GENES

(75) Inventor: Stephen J. Brown, San Mateo, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 0 days.

(21) Appl. No.: 09/496,893

(22) Filed: Feb. 2, 2000

Related U.S. Application Data

(63) Continuation of application No. 09/041,809, filed on Mar. 13, 1998, now abandoned, which is a continuation-in-part of application No. 08/946,341, filed on Oct. 7, 1997, now Pat. No. 5,997,476, which is a continuation-in-part of application No. 08/847,009, filed on Apr. 30, 1997, now Pat. No. 5,897,493, application No. 09/496,893, and a continuation-in-part of application No. 09/378,188, filed on Aug. 20, 1999, now abandoned, which is a continuation of application No. 08/850,840, filed on May 3, 1997, now Pat. No. 5,985,559, which is a continuation of application No. 08/847,009, filed on Apr. 30, 1997, now Pat. No. 5,897,493.

(60) Provisional application No. 60/041,746, filed on Mar. 28, 1997, provisional application No. 60/041,751, filed on Mar. 28, 1997.

(51) Int. Cl.
*G01N 33/48* (2006.01)

(52) U.S. Cl. ............... 702/19; 706/11; 706/48; 707/722; 707/737; 707/776; 707/805; 435/6; 600/301

(58) Field of Classification Search ...... 435/6; 436/501; 514/2, 44
See application file for complete search history.

(56) References Cited

U.S. PATENT DOCUMENTS

| | | |
|---|---|---|
| 3,426,150 A | 2/1969 | Tygart |
| 3,566,365 A | 2/1971 | Rawson et al. |
| 3,566,370 A | 2/1971 | Worthington, Jr. et al. |
| 3,581,072 A | 5/1971 | Nymeyer |
| 3,768,014 A | 10/1973 | Smith |
| 3,811,116 A | 5/1974 | Takeuchi et al. |
| 3,883,235 A | 5/1975 | Lynn et al. |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. et al. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A | 3/1988 | Allen, III |
| 4,738,451 A | 4/1988 | Logg |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |

(Continued)

FOREIGN PATENT DOCUMENTS

EP 0286456 10/1988

(Continued)

OTHER PUBLICATIONS

Martinez, Am. J. Respir. Crit. Care Med., vol. 156, pp. S117-S122, 1997.*

Kauffman et al., Am. J. Respir. Crit. Care Med., vol. 156, pp. S123-S129, 1997.*

Schork, Am. J. Respir. Crit. Care Med., vol. 156, pp. S103-S109, 1997.*

"AdOptimizer—Ad Management Software for Websites", Newsbytes, pNEW10040041, Oct. 4, 1996.

"Blood Glucose Monitors", Portable Health Device, (1998), vol. 17(9), pp. 253-271.

"Cathay Pacific Airways—USA receives more than 1,300 bids during first five days of CyberAuction"; Business Wire, Oct. 18, 1995, p. 10181119.

(Continued)

*Primary Examiner* — Carolyn L. Smith

(74) *Attorney, Agent, or Firm* — Christopher P. Maiorana, PC

(57) ABSTRACT

The present invention describes a system and method of using individuals' behavioral and physiologic information to identify disease-influencing genes.

17 Claims, 18 Drawing Sheets

U.S. PATENT DOCUMENTS

| | | |
|---|---|---|
| 4,799,156 A | 1/1989 | Shavit et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,916,441 A | 4/1990 | Gombrich |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,552 A | 7/1992 | Fang et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips et al. |
| 5,307,263 A | 4/1994 | Brown |
| 5,309,919 A | 5/1994 | Snell et al. |
| 5,321,009 A | 6/1994 | Baeder et al. |
| 5,325,288 A | 6/1994 | Satou |
| 5,329,459 A | 7/1994 | Kaufman et al. |
| 5,329,608 A | 7/1994 | Bocchieri et al. |
| 5,331,549 A | 7/1994 | Crawford, Jr. |
| 5,333,981 A | 8/1994 | Pronovost et al. |
| 5,335,338 A | 8/1994 | Proesel |
| 5,339,821 A | 8/1994 | Fujimoto |
| 5,341,291 A | 8/1994 | Roizen et al. |
| 5,343,239 A | 8/1994 | Lappington et al. |
| 5,344,324 A | 9/1994 | O'Donnell et al. |
| 5,357,427 A | 10/1994 | Langen et al. |
| 5,366,896 A | 11/1994 | Margrey et al. |
| 5,368,562 A | 11/1994 | Blomquist et al. |
| 5,371,687 A | 12/1994 | Holmes, II et al. |
| 5,375,604 A | 12/1994 | Kelly et al. |
| 5,377,100 A | 12/1994 | Pope et al. |
| 5,390,238 A | 2/1995 | Kirk et al. |
| 5,399,821 A | 3/1995 | Inagaki et al. |
| 5,410,471 A | 4/1995 | Alyfuku et al. |
| 5,410,474 A | 4/1995 | Fox |
| 5,429,140 A | 7/1995 | Burdea et al. |
| 5,431,690 A | 7/1995 | Schaldach et al. |
| 5,431,691 A | 7/1995 | Snell et al. |
| 5,434,611 A | 7/1995 | Tamura |
| 5,438,607 A | 8/1995 | Przygoda, Jr. et al. |
| 5,438,983 A | 8/1995 | Falcone |
| 5,441,047 A | 8/1995 | David et al. |
| 5,449,334 A | 9/1995 | Kingsbury |
| 5,454,721 A | 10/1995 | Kuch |
| 5,454,722 A | 10/1995 | Holland et al. |
| 5,456,606 A | 10/1995 | McIntyre |
| 5,456,692 A | 10/1995 | Smith, Jr. et al. |
| 5,458,123 A | 10/1995 | Unger |
| 5,467,269 A | 11/1995 | Flaten |
| 5,471,039 A | 11/1995 | Irwin, Jr. et al. |
| 5,471,382 A | 11/1995 | Tallman et al. |
| 5,483,276 A | 1/1996 | Brooks et al. |
| 5,488,412 A | 1/1996 | Majeti et al. |
| 5,488,423 A | 1/1996 | Walkingshaw et al. |
| 5,501,231 A | 3/1996 | Kaish |
| 5,502,636 A | 3/1996 | Clarke |
| 5,502,726 A | 3/1996 | Fischer |
| 5,504,519 A | 4/1996 | Remillard |
| 5,517,405 A | 5/1996 | McAndrew et al. |
| 5,518,001 A | 5/1996 | Snell |
| 5,519,058 A | 5/1996 | Gonick et al. |
| 5,519,433 A | 5/1996 | Lappington et al. |
| 5,523,232 A | 6/1996 | Sechler |
| 5,536,249 A | 7/1996 | Castellano et al. |
| 5,542,420 A | 8/1996 | Goldman et al. |
| 5,544,649 A | 8/1996 | David et al. |
| 5,546,943 A | 8/1996 | Gould |
| 5,549,117 A | 8/1996 | Tacklind et al. |
| 5,550,575 A | 8/1996 | West et al. |
| 5,553,609 A | 9/1996 | Chen et al. |
| 5,558,638 A | 9/1996 | Evers et al. |
| 5,564,429 A | 10/1996 | Bornn et al. |
| 5,569,212 A | 10/1996 | Brown |
| 5,572,421 A | 11/1996 | Altman et al. |
| 5,572,646 A | 11/1996 | Kawai et al. |
| 5,574,828 A | 11/1996 | Hayward et al. |
| 5,576,952 A | 11/1996 | Stutman et al. |
| 5,583,758 A | 12/1996 | McIlroy et al. |
| 5,590,648 A | 1/1997 | Mitchell et al. |
| 5,593,349 A | 1/1997 | Miguel et al. |
| 5,593,390 A | 1/1997 | Castellano et al. |
| 5,594,637 A | 1/1997 | Eisenberg et al. |

| | | | | | | |
|---|---|---|---|---|---|---|
| 5,596,994 A | 1/1997 | Bro | | 5,835,896 A | 11/1998 | Fisher et al. |
| 5,597,307 A | 1/1997 | Redford et al. | | 5,840,020 A | 11/1998 | Heinonen et al. |
| 5,601,435 A | 2/1997 | Quy | | 5,842,976 A | 12/1998 | Williamson |
| 5,613,495 A | 3/1997 | Mills et al. | | 5,868,669 A | 2/1999 | Iliff |
| 5,619,991 A | 4/1997 | Sloane | | 5,868,683 A | 2/1999 | Protopapas et al. |
| 5,624,265 A | 4/1997 | Redford et al. | | 5,875,432 A | 2/1999 | Sehr |
| 5,628,309 A | 5/1997 | Brown | | 5,879,163 A | 3/1999 | Brown et al. |
| 5,629,981 A | 5/1997 | Nerlikar | | 5,882,338 A | 3/1999 | Gray |
| 5,631,844 A | 5/1997 | Margrey et al. | | 5,887,133 A | 3/1999 | Brown et al. |
| 5,633,910 A | 5/1997 | Cohen | | 5,893,077 A | 4/1999 | Griffin |
| 5,635,532 A | 6/1997 | Samid | | 5,893,098 A | 4/1999 | Peters et al. |
| 5,640,569 A | 6/1997 | Miller et al. | | 5,897,493 A | 4/1999 | Brown |
| 5,640,953 A | 6/1997 | Bishop et al. | | 5,899,855 A | 5/1999 | Brown |
| 5,642,731 A | 7/1997 | Kehr | | 5,911,687 A | 6/1999 | Sato et al. |
| 5,642,936 A | 7/1997 | Evans | | 5,913,310 A | 6/1999 | Brown |
| 5,651,363 A | 7/1997 | Kaufman et al. | | 5,918,603 A | 7/1999 | Brown |
| 5,651,775 A | 7/1997 | Walker et al. | | 5,920,477 A | 7/1999 | Hofbert et al. |
| 5,659,691 A | 8/1997 | Durward et al. | | 5,933,136 A | 8/1999 | Brown |
| 5,666,487 A | 9/1997 | Goodman et al. | | 5,935,060 A | 8/1999 | Iliff |
| 5,670,711 A | 9/1997 | Detournay et al. | | 5,940,801 A | 8/1999 | Brown |
| 5,675,635 A | 10/1997 | Vos et al. | | 5,941,829 A | 8/1999 | Saltzstein et al. |
| 5,678,562 A | 10/1997 | Sellers | | 5,945,651 A | 8/1999 | Chorosinski et al. |
| 5,678,571 A | 10/1997 | Brown | | 5,950,630 A * | 9/1999 | Portwood et al. ............ 128/897 |
| 5,679,075 A | 10/1997 | Forrest et al. | | 5,951,300 A | 9/1999 | Brown |
| 5,680,590 A | 10/1997 | Parti | | 5,954,641 A | 9/1999 | Kehr et al. |
| 5,680,866 A | 10/1997 | Kangas et al. | | 5,956,501 A | 9/1999 | Brown |
| 5,687,322 A | 11/1997 | Deaton et al. | | 5,960,403 A | 9/1999 | Brown |
| 5,687,717 A | 11/1997 | Halpern et al. | | 5,961,446 A | 10/1999 | Beller et al. |
| 5,687,734 A | 11/1997 | Dempsey et al. | | 5,966,526 A | 10/1999 | Yokoi |
| 5,689,652 A | 11/1997 | Lupien et al. | | 5,971,855 A | 10/1999 | Ng |
| 5,692,906 A | 12/1997 | Corder | | 5,971,922 A | 10/1999 | Arita et al. |
| 5,704,364 A | 1/1998 | Saltzstein et al. | | 5,983,003 A | 11/1999 | Lection et al. |
| 5,704,366 A | 1/1998 | Tacklind et al. | | 5,983,217 A | 11/1999 | Khosravi-Sichani et al. |
| 5,704,902 A | 1/1998 | Vandenbelt et al. | | 5,987,471 A | 11/1999 | Bodine et al. |
| 5,704,922 A | 1/1998 | Brown | | 5,995,969 A | 11/1999 | Lee et al. |
| 5,710,178 A | 1/1998 | Samid | | 5,997,476 A | 12/1999 | Brown |
| 5,710,918 A | 1/1998 | Lagarde et al. | | 5,997,502 A | 12/1999 | Reilly et al. |
| 5,711,297 A | 1/1998 | Iliff | | 6,001,065 A | 12/1999 | DeVito |
| 5,714,319 A | 2/1998 | Joutel et al. | | 6,022,315 A | 2/2000 | Iliff |
| 5,715,451 A | 2/1998 | Marlin | | 6,022,615 A | 2/2000 | Rettenbacher |
| 5,715,823 A | 2/1998 | Wood et al. | | 6,023,686 A | 2/2000 | Brown |
| 5,717,739 A | 2/1998 | Dyer et al. | | 6,024,281 A | 2/2000 | Shepley |
| 5,717,913 A | 2/1998 | Driscoll | | 6,029,138 A | 2/2000 | Khorasani et al. |
| 5,720,733 A | 2/1998 | Brown | | 6,032,119 A | 2/2000 | Brown et al. |
| 5,722,418 A | 3/1998 | Bro | | 6,035,328 A | 3/2000 | Soukal |
| 5,727,153 A | 3/1998 | Powell | | 6,046,761 A | 4/2000 | Echerer |
| 5,730,124 A | 3/1998 | Yamauchi | | 6,049,794 A | 4/2000 | Jacobs et al. |
| 5,730,654 A | 3/1998 | Brown | | 6,050,940 A | 4/2000 | Braun et al. |
| 5,732,696 A | 3/1998 | Rapoport et al. | | 6,055,314 A | 4/2000 | Spies et al. |
| 5,732,709 A | 3/1998 | Tacklind et al. | | 6,055,487 A | 4/2000 | Margery et al. |
| 5,734,413 A | 3/1998 | Lappington et al. | | 6,055,506 A | 4/2000 | Frasca, Jr. |
| 5,749,083 A | 5/1998 | Koda et al. | | 6,057,758 A | 5/2000 | Dempsey et al. |
| 5,752,234 A | 5/1998 | Withers | | 6,068,615 A | 5/2000 | Brown et al. |
| 5,754,740 A | 5/1998 | Fukuoka et al. | | 6,095,985 A | 8/2000 | Raymond et al. |
| 5,760,771 A | 6/1998 | Blonder et al. | | 6,101,478 A | 8/2000 | Brown |
| 5,772,585 A | 6/1998 | Lavin et al. | | 6,108,635 A * | 8/2000 | Herren et al. .................... 705/2 |
| 5,778,882 A | 7/1998 | Raymond et al. | | 6,110,148 A | 8/2000 | Brown et al. |
| 5,782,814 A | 7/1998 | Brown et al. | | 6,113,578 A | 9/2000 | Brown |
| 5,785,650 A | 7/1998 | Akasaka et al. | | 6,138,145 A | 10/2000 | Kawanaka |
| 5,787,295 A | 7/1998 | Nakao | | 6,144,837 A | 11/2000 | Quy |
| 5,791,342 A | 8/1998 | Woodard | | 6,151,586 A | 11/2000 | Brown |
| 5,792,117 A | 8/1998 | Brown | | 6,161,095 A | 12/2000 | Brown |
| 5,793,969 A | 8/1998 | Kamentsky et al. | | 6,167,362 A | 12/2000 | Brown et al. |
| 5,794,219 A | 8/1998 | Brown | | 6,167,386 A | 12/2000 | Brown |
| 5,794,251 A | 8/1998 | Watanabe et al. | | 6,168,563 B1 | 1/2001 | Brown |
| 5,796,393 A | 8/1998 | MacNaughton | | 6,177,940 B1 | 1/2001 | Bond et al. |
| 5,799,318 A | 8/1998 | Cardinal et al. | | 6,186,145 B1 | 2/2001 | Brown |
| 5,800,458 A | 9/1998 | Wingrove | | 6,189,029 B1 | 2/2001 | Fuerst |
| 5,802,494 A | 9/1998 | Kuno | | D439,242 S | 3/2001 | Brown et al. |
| 5,802,534 A | 9/1998 | Hatayama et al. | | 6,210,272 B1 | 4/2001 | Brown |
| 5,806,057 A | 9/1998 | Gormley et al. | | 6,221,012 B1 | 4/2001 | Maschke et al. |
| 5,810,747 A | 9/1998 | Brudny et al. | | 6,233,539 B1 | 5/2001 | Brown |
| 5,819,735 A | 10/1998 | Mansfield et al. | | 6,240,393 B1 | 5/2001 | Brown |
| 5,822,544 A | 10/1998 | Chaco et al. | | 6,248,065 B1 | 6/2001 | Brown |
| 5,822,715 A | 10/1998 | Worthington et al. | | 6,260,022 B1 | 7/2001 | Brown |
| 5,825,283 A | 10/1998 | Camhi | | 6,270,455 B1 | 8/2001 | Brown |
| 5,827,180 A | 10/1998 | Goodman | | 6,270,456 B1 | 8/2001 | Iliff |
| 5,828,943 A | 10/1998 | Brown | | 6,334,778 B1 | 1/2002 | Brown |
| 5,832,448 A | 11/1998 | Brown | | 6,352,523 B1 | 3/2002 | Brown et al. |

| | | |
|---|---|---|
| 6,368,273 B1 | 4/2002 | Brown |
| 6,370,513 B1 | 4/2002 | Kolawa et al. |
| 6,375,469 B1 | 4/2002 | Brown |
| 6,379,301 B1 | 4/2002 | Worthington et al. |
| 6,381,577 B1 | 4/2002 | Brown |
| 6,436,036 B1 | 8/2002 | Miller-Kovach et al. |
| 6,513,532 B2 | 2/2003 | Mault et al. |
| 6,678,669 B2* | 1/2004 | Lapointe et al. ............... 706/15 |
| 2002/0019748 A1 | 2/2002 | Brown |
| 2003/0068649 A1* | 4/2003 | Doberstein et al. ............ 435/7.1 |
| 2004/0106855 A1 | 6/2004 | Brown |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |

FOREIGN PATENT DOCUMENTS

| | | |
|---|---|---|
| EP | 0320749 | 6/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 5/1995 |
| EP | 676709 | 10/1995 |
| EP | 680727 | 11/1995 |
| EP | 761160 | 3/1997 |
| EP | 08131551 | 12/1997 |
| EP | 0251520 | 1/1998 |
| GB | 2218831 | 11/1989 |
| GB | 2225637 | 6/1990 |
| JP | 54005785 | 1/1979 |
| JP | 54146633 | 11/1979 |
| JP | 62226278 | 10/1987 |
| JP | 5155024 | 6/1993 |
| JP | 5266002 | 10/1993 |
| JP | 1995407095963 | 4/1995 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9831275 | 7/1998 |
| WO | WO-9839933 | 9/1998 |

OTHER PUBLICATIONS

"Cathay Pacific Airways—USA to Hold First-Ever Internet CyberAuction; CyberTravelers Can Bid for 50 Business Class Round Trips to Hong Kong—No Minimum Bid"; Business Wire; p. 9261084; Sep. 26, 1995; Dialog: File 148, Acc#08167091.
"Central Fetal Monitoring Systems with Optical Disk Storage", New Technology Brief, (Nov./Dec. 1998), vol. 2, No. 6, pp. 249-251.
"Digital Doggie"; retrieved from URL http://www.virtualpet.com/vp/farm/gigapet/ddoggie.htm Apr. 23, 2000.
"European Search Report", From 6858P005EP, (Mar. 27, 1998).
"Future of the Virtual Pet Industry," 1997 [retrieved on Apr. 23, 2000], Retrieved from <URL:www.virtualpet.com/vp/ future/future.htm>.
"Giga Farm"; retrieved from URL http://www.virtualpet.com/vp/farm/gigapet/gpfarm/gpfarm.htm Apr. 23, 2000.
"Giga Pets," 1997 [retrieved on Apr. 23, 2000], Retrieved from <URL:www.virtualpet.com/vp/farm/gigapet/gigapet.htm>.
"How Flash Memory Works", Internet printout of URL address: http://www.howstuffworks.com/flash-memory4.htm, (Sep. 28, 2002), 2 pages.
"Introducing the Next Generation of About Your Diabetes", U.S. Pharmacopical Convention and American Diabetes Association, (1993).
"Nano Baby Instructions"; retrieved from file://C:\My Documents\Nano Baby Instructions.htm Apr. 23, 2000.
"Nano Fighter Pets"; retrieved from URL http://www.virtualpet.com/vp/farm/nano/nfighter.htm Apr. 23, 2000.
"New Horizons teams with Duke, Real Media"; The Seybold Report on Desktop Publishing, v10 n12 p. 24(1), Aug. 12, 1996.
"Onsale Joins Fray as Online Shopping Picks Up Speed: Internet Booms"; Computer Reseller News; Jun. 5, 1995; p. 73; Dialog: File 16, Acc#05649796.
"ONSALE Onsale Brings Thrill of Auctions and Bargain Hunting Online; Unique Internet retail service debuts with week-long charity auction for The Computer Museum in Boston", May 24, 1995; Dialog Abstract: File 610, Acc#0489267.
"Playmates Toys deals knockout blow to virtual pet competitors with introduction of Nano Fighter™ For Boys"; New Nano Pet Fighting Pet Press Release; retrieved from URL http://www.virtualpet.com/vp/farm/nano/nfightpr.htm Apr. 23, 2000.
"Playmates Toys leads Americas virtual pet craze into its next generation by introducting talking Nano Pals"; Talking Nano Pet Press Release; Nov. 18, 1997; retrieved from URL http://www.virtualpet.com/vp/farm/nano/talkn/tnpress.htm on Apr. 23, 2000.
"Putting the Lot on the Net", Antique Collector, vol. 66, Issue 9, p. 26, Downloaded from Corporate Resource Net, Nov./Dec. 1995.
"Talking Nano Puppy"; retrieved from URL http://www.virtualpet.com/vp/farm/nano/talkn/talkn.htm Apr. 23, 2000.
"Tamagotchi," 1997 [retrieved on Apr. 23, 2000], Retrieved from <URL:www.virtualpet.com/vp/farm/lleg/lleg.htm>.
"The description of the Tandy Radio Shack TRS-80 Model 100/102 device available at http://www.old-computuers.com/musuem/computer.asp?c=233", World Wide Web, (Feb. 13, 2004), 1-3.
"Theme Hospital," product review 1996 [retrieved Apr. 21, 2000], Retrieved from <URL:www.vigilante.co.uk/ep/misc/hospital.htm>.
"Towards a partnership of care", M2 Presswire, Jun. 14, 2000.
"Virtual Pet Product Reviews," 1997 [retrieved on Apr. 23, 2000], Retrieved from <URL:www.virtualpet.com/vp/farm/reviews/reviews,htm>.
"Virtual Tomagutchi," 1998 [retrieved Apr. 23, 2000], Retrieved from <URL:www.sttf.org/english/action/tomagutchi.html>.
"Who Will Dominate the Desktop in the 90's?", Jack Shandle, Electronics, Feb. 1990, pp. 48-50. (3 pages).
Adilman; "Videogames: Knowing the Score"; Creative Computing; v9; p. 224(5); Dec. 1983; Dialog: File 148, Acc# 01891055.
Anonymous, "Health Hero Network, Inc. Receives First-Ever FDA Clearance for Connecting Medical Devices to Internet", PR Newswire, (Dec. 2, 1993), 3 pages.
Bai, "Design of home healthcare network", IEEE 1997 pp. 1657-1658.
Billiard, A., et al. "Telematic Transmission of Computerized Blood Glucose Profiles for IDDm Patients", Diabetes Care, (Feb. 1991), vol. 14, No. 2, pp. 130-134.
Bower, "Brain Clues to Energy-efficient Learning", Science News, (Apr. 1992), v. 141; p. 215(1); Dialog: File 647, Acct# 12123949.
Brenman et al.; "Interaction of Nitric Oxide Synthase with the Postsynaptic Density Protein PSD-95 and $\alpha$1-Syntrophin Mediated by PDZ Domains"; Cell; vol. 84, pp. 757-767, Mar. 8, 1996; Ref: XP-002104701.
Bruce, "Health Hero Network CEO, CNNfn", Digital Jam, (Dec. 1, 1999), 3.
Bruce, et al., "The Effects of Sympathetic Nervous System Activation and Psychological Stress . . . "; Diabetologia; 35(9); 1992; 835-843; Dialog: File 5, Acc#9629427. (9 pages).
Brunetti, P., et al., "A Simulation Study on a Self-Turning Portable Controller of Blood Glucose", The International Journal of Artificial Organs, (1993), vol. 16, No. 16, pp. 51-57.
Caprihan, A., et al., "A Simple Microcomputer for Biomedical Signal Processing", IECI '78 Annual Conference Proceedings on Industrial Applications of Microprocessors, (Mar. 20, 1978), 18-23.
Cheng, Joe H., "PCT Search Report", (Jan. 11, 1996).
DigiPet Instruction Manual, 1997.

Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.

Edelson; "Fashion Reevaluates Flickering Fortunes of TV Home Shopping"; WWD; v170 n87; p1(3); Nov. 8, 1995; Dialog: File 148, Acc#08289119.

Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.

Finston, "Parent + Teacher = Healthy Child", Diabetes Forecast, (Apr. 1994), v47 n9; P26(5); Dialog: file 149, Acc# 15804228.

Fox, "Not My Type: Type B Behavior, Type I Diabetes Plus Stress Equals Blood Sugar Blues", Health, (Mar. 1998), v20 n3; pp. 22(1); Dialog: File 149, Acc# 06397959.

Franklin; "Proposed Auction Rules for PCS: The FCC Plans to Use Competitive Bidding, but Exact Procedures are Undefined"; Cellular Business; v10 n13; p. 18(2); Dec. 1993; Dialog: File 148, Acc#06787310.

Frieberger, Paul, "Video Game Takes on Diabetes Superhero 'Captain Novolin' Offers Treatment Tips", San Francisco Examiner, (Jun. 26, 1992), Fourth Edition, Business Section B1.

Furnham, et al; "Measuring Locus of Control: a Critique of General Children's Health-and Work-related Locus of Control Questionnaires"; British Journal of Psychology; v84 n4; p. 443(37); Nov. 1993; Dialog: File 88, Acc# 14903135.

Gardner, et al.; "Comprehension and Appreciation of Humorous Material Following Brain Damage"; Brain; Sep. 1975; 98(3); pp. 399-412; Dialog: File 153, Acc#02859983. (14 pages).

Gauntlet (for PC) rulebook by Mindscape Inc. (Gauntlet by Apple);1985.

Giuffrida, et al., Should We Pay the Patient? Review of Financial Incentives to enhance Patient Compliance:, Biomedical Journal, (1997), vol. 315, pp. 703-707.

Gordon; "Auctions Become High Tech"; Dealer Business; v29 n7; p. 21(4); Mar. 1995; Dialog: File 148, Acc#07862519.

Hauben, Jay R., "A Brief History of the Cleveland Free-Net", available at http://www.ais.org/~irh/acn7-1.a09.html, (1995) pp. 1-4.

Hauser, et al., "Will Computers Replace or Complement the Diabetes Educator?", The Medical Journal of Australia, (Oct. 5, 1992), vol. 157, 489-491.

Horio, Hiroyuki, et al., "Clinical Telecommunication Network System for Home Monitoring", Medical & Biological Engineering & Computing, (Mar. 1994), vol. 32, 227-230.

Howey, et al., "A Rapidly Absorbed Analogue of Human Insulin"; Diabetes, vol. 43, Mar. 1994, pp. 396-402. (7 pages).

Hunter, "Technological Advances in Bedside Monitoring: Biosensors", Archives and Laboratory Medicine, (Jul. 1987), pp. 633-636.

Hutheesing, Nikhil, "An on-line gamble", Forbes, v157 n10 p. 288(1), May 20, 1996.

Jaffrey et al.; "PIN: An Associated Protein Inhibitor of Neuronal Nitric Oxide Synthase"; Science; vol. 274; Nov. 1, 1996; Ref: XP 002050141.

Jimison et al., "Patient-Specific explanation in models of chronic disease", Revised Feb. 1992 Artificial Intelligence in Medicine 4 (1992) 191-205.

Jones, Chris, "Microsoft readies DocObject; technology will allow document editing in Web browsers", InfoWorld, v18 n18 p. 48(1), Apr. 29, 1996.

Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.

Kaufman, Steven, B., "The Learning Game", Nation's Business, (Nov. 1993).

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.

Lachnit, Carroll, "Hawkin's Online Auction", Photo District News, vol. 16, Issue 1, p. 18, Jan. 1996.

Lacyk, John, "PCT Search Report", (Jun. 12, 1997).

Latman, N.S., "Evaluation of Electronic, Digital Blood Glucose Monitors", Biomedical Instrumentation and Technology, (1991), vol. 25, No. 1, 43-49.

Leyerle, Beverly J., et al., "The PDMS as a Focal Point for Distributed Patient Data", International Journal of Clinical Monitoring and Computing, (1988), vol. 5, pp. 155-161.

Luebke, Cathy, "Barrett-Jackson Auction Turns High-Tech", Business Journal, vol. 16, Issue 12, pp. 11, Jan. 19, 1996.

M.U.L.E. rulebook by Electronic Arts, 1983.

Makikawa, M., et al., "Microprocessor-Based Memory Device for Ambulatory Heart Rate and Physical Activity Recording", Methods of Information in Medicine, (1994), vol. 33, No. 1, pp. 94-96.

Marsh, David G. "Approaches Toward the Genetic Analysis of Complex Traits Asthma and Atrophy", Am. J. Respir.Crit.Care Med., (1997), vol. 156, pp. S-133-S138.

Martinez, Fernando D., "Complexities of the Genetics of Asthma", Am.J. Respir. Crit. Care Med., (1997), vol. 156, pp. S117-S122.

Marx, Wendy, "More than just the Scores: ESPNET SportsZone is a model for expanding brand names online", InformationWeek, n576 p. 61(2), Apr. 22, 1996.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

Meissner, et al., "Building an Integrated Clinical and Research Network", Proceedings of the SPIE, (Oct. 24, 1995), vol. 2618, p. 92-99.

Miles, Laughton E., "A Portable Microcomputer for Long-Term Physiological Monitoring in the Home and Work Environment", Medical Monitoring in the Home and Work Environment, (1990), pp. 47-57.

Mims; "Psychological Testing"; Computers & Electronics; v23; p. 22(6); Feb. 1985; Dialog: File 47, Acc# 2654858.

Moore, "New Applications Break Through Storage Boundaries", Computer Technology Review, (Oct. 1999), vol. 19, No. 10 p. 1.

Nano Page, 1997 [retrieved on Apr. 23, 2000], Retrieved from <URL:www.virtualpet.com/vp/farm/nano/nano.htm>.

O'Donnell; "Alan's At It Again"; Bond Buyer; v309 n29448; p. 1(3); Jul. 21, 1994; Dialog: File 148, Acc#07478152.

Octogotchi Instruction Manual, 1997. Dino-Kun Instruction Manual, 1997.

Pfeiffer, E. F., "The Glucose Sensor. The Missing Link in Diabetes Therapy", Hormone and Metabolic Research, (1990), vol. 24m Suppl. pp. 154-164.

Poitout, V., et al. "A Glucose Monitoring Systerri for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Polson, Gary "Recent Developments and Trends in Keychain Virtual Pets," 1997 [retrieved on Apr. 23, 2000], Retrieved from <URL:www.virtualpet.com/vp/future/trends1a.htm>.

Potter, David, "Fundamentals of PC-Based Data Acquisition", Sensors, (Feb. 1994), pp. 12-20.

Reis, H, "Telemedicine: Transmitting Expertise to the Point of Care Toward an Electronic Patient Record"; '97, Nashville, TN, Apr. 27-May 3, 1997, pp. 248-256, v. 3.

Research project launched to improve health of America's communities; new Disney community in Florida is focus of program. Business Wire, p. 10011142. Oct. 1, 1996.

RO_AUCTION Auctioneers Property Database System and RO_AUCTION Auctioneers Accounting System; RO-AUCTION features; Dec. 4, 1995.

Roberts; "Diabetes and Stress: A Type A Connection?", Psychology Today, (Jul. 1987), v. 21; pp. 22(1); Dialog: File 149, Acc# 05038381.

Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.

Schement, "An Intelligent Controller for Neurophysiological Experiments," Proceeding of the Annual Symposium on Computer Based Medical Systems, Durham, Jun. 14-17, 1992, p. 528, line 1—p. 529, line 21.

Schenkels, P., "Supplementary European Search Report", Application No. EP 97 92 2716, (Mar. 11, 2002).

Schork, Nicholas J., "Genetics of Complex Disease", Am.J.Respir. Crit. Care Me., (1997), vol. 156, pp. S103-S109.

Schrezenmeir, J. et al., "Computer Assisted Insulin Dosage Adjustment—Perspective for Diabetes Control", Hormone and Metabolic Research, Supplement Series, (1990), vol. 24, pp. 116-123.

Shandle, Jack, "Who will dominate the desktop in the 90's?", Electronics, (Feb. 1990), pp. 48-50.

Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.

Siegmann;"Nowhere to Go but Up"; PC Week; v12 n42, p. A5(1); Oct. 23, 1995; Dialog: File 148, Acc#08222496.

Soeldner, J. S., "Treatment of Diabetes Mellitus by Devices", The American Journal of Medicine, (Jan. 1981), vol. 70, 183-194.

Spitzer et al.; "The moderating effect of age on self-care"; Western Journal of Nursing Research, v18, n2, p. 136(13), Apr. 1996.

Telemedicine Provides Two-Way Computer Link for Parents of Very Premature Infants. PR Newswire. p. 1007NEM034. Oct. 7, 1996.

United Healthcare's OPTUM Division goes online to better health by announcing a unique internet application. PR Newswire, p0801MNTH004. Aug. 1, 1996.

Updike, Stuart J., et al., "Laboratory Evaluation of New Reusable Blood Glucose Sensor", Diabetes Care, (Nov./Dec. 1998), vol. 11, No. 10, pp. 801-807.

Valla, et al., "A Structured Pictorial Questionnaire to Assess DSM-III-R-based Diagnosis in Children (6-11 years)", Journal of Abnormal Child Psychology; v22 n4; p. 403(21); Aug. 1994; Dialog: File 88, Acc# 15759542.

Vallera, D. A., et al., "Accuracy of Portable Blood Glucose Monitoring", American Journal of Clinical Pathology, (1991), vol. 95, No. 2, pp. 247-252.

Voelker, Rebecca, "Shoe Leather Therapy is Gaining on TB", Jama, (Mar. 13, 1996), vol. 275, 743.

Wilkins, Aaron. "Expanding Internet access for health care consumers", Health Care Management Review, Summer, Jul. 1999, 24-30.

Wyatt, J. C., "Clinical Data Systems, Part 2: Components and Techniques", Lancet, (Dec. 1994), vol. 344, No. 8937, pp. 1609-1614.

Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.

* cited by examiner

NUMBER: 9001 {LF}

LED: 1 {LF}

ZAP: {LF}

CLS: {LF}

DISPLAY: ANSWER QUERIES NOW?
        PRESS ANY BUTTON TO START {LF}

WAIT: {LF}

CLS: {LF}

DISPLAY: HOW OLD WERE YOU WHEN YOU
        WERE DIAGNOSED WITH NIDDM?
        <20    20-30    30-40    >40 {LF}

INPUT: OOOO {LF}

CLS: {LF}

DISPLAY: ARE YOU OVERWEIGHT?
        YES   NO {LF}

INPUT: OOOO {LF}

CLS: {LF}

DISPLAY: WHAT IS YOUR CHOLESTEROL LEVEL?
        <200    200-250    250-300   >300
        mg/dL   mg/dL     mg/dL    mg/dL {LF}

INPUT: OOOO {LF}

CLS: {LF}

DISPLAY: DO YOU SMOKE?
        YES   NO {LF}

*Fig. 6A*

INPUT: OOOO {LF}

CLS: {LF}

DISPLAY: CONNECT GLUCOSE METER
AND PRESS ANY BUTTON
WHEN FINISHED {LF}

WAIT: {LF}

CLS: {LF}

DISPLAY: COLLECTING MEASUREMENTS {LF}

COLLECT: GLUCOSE_METER {LF}

CLS: {LF}

DISPLAY: CONNECT APPARATUS TO
TELEPHONE JACK AND PRESS ANY
BUTTON WHEN FINSIHED {LF}

WAIT: {LF}

LED: 0 {LF}

CLS: {LF}

DELAY: 03:00 {LF}

DISPLAY: CONNECTING TO SERVER {LF}

CONNECT: {LF}

{EOF}

*Fig. 6B*

PATIENT REPORT

PATIENT: LINDSEY, DAN ▽

DATE OF MEASUREMENT: MARCH 15, 1997 ▽

QUERY RESPONSES

HOW OLD WERE YOU WHEN YOU WERE DIAGNOSED WITH NIDDM?
30-40

ARE YOU OVERWEIGHT?
YES

WHAT IS YOUR CHOLESTEROL LEVEL?
250-300 mg/dL

DO YOU SMOKE?
NO

MG/DL vs HOURS (6–24)

*Fig. 10*

| NIDDM DATA TABLE | | 150 |
|---|---|---|
| INDIVIDUAL NO: _____ | | 151 |
| 152<br>NAME<br>FIELD | 154<br>VALUE<br>FIELD | 156<br>EXPLANATION |
| AGE WHEN<br>DIAGNOSED<br>WITH NIDDM? | <20 = 0<br>20-30 = 25<br>30-40 = 50<br>>40 = 100 | TO DETERMINE<br>IF CONDITION IS<br>CAUSED BY AGE |
| OVERWEIGHT<br>OR<br>NON-OVERWEIGHT? | OVERWT = 50<br><br>NONOVERWT<br>=0 | TO DETERMINE<br>IF CONDITION IS<br>CAUSED BY<br>WEIGHT |
| CHOLESTEROL LEVEL? | <200 = 0<br>200-250 = 25<br>250-300 = 50<br>>300 = 100 | TO DETERMINE<br>IF CONDITION IS<br>CAUSED BY<br>CHOLESTEROL LEVEL |
| SMOKING<br>OR<br>NON-SMOKING? | SMOKING = 50<br><br>NON-SMOKING<br>= 0 | TO DETERMINE<br>IF CONDITION IS<br>CAUSED BY<br>NICOTINE |

*Fig. 13*

| NIDDM DATA TABLE | | 150 |
|---|---|---|
| INDIVIDUAL NO: 64025 | | 151 |
| 152<br>NAME<br>FIELD | 154<br>VALUE<br>FIELD | 156<br>EXPLANATION |
| AGE WHEN DIAGNOSED WITH NIDDM? | 35-40 = 50 | TO DETERMINE IF CONDITION IS CAUSED BY AGE |
| OVERWEIGHT OR NON-OVERWEIGHT? | OVERWT = 50 | TO DETERMINE IF CONDITION IS CAUSED BY WEIGHT |
| CHOLESTEROL LEVEL? | 250-300 = 50 | TO DETERMINE IF CONDITION IS CAUSED BY CHOLESTEROL LEVEL |
| SMOKING OR NON-SMOKING? | NON-SMOKING = 0 | TO DETERMINE IF CONDITION IS CAUSED BY NICOTINE |

*Fig. 14*

CONCLUDE: NIDDM NOT RELATED TO WEIGHT, LIKELY RELATED TO GENE SEQUENCE A

SYSTEM AND METHOD FOR IDENTIFYING DISEASE-INFLUENCING GENES

RELATED APPLICATION INFORMATION

This application is a continuation of application Ser. No. 09/041,809 filed Mar. 13, 1998, now abandoned, which is a continuation-in-part of application Ser. No. 08/946,341 filed Oct. 7, 1997, now U.S. Pat. No. 5,997,476, which is a continuation-in-part of application Ser. No. 08/847,009 filed Apr. 30, 1997, now U.S. Pat. No. 5,897,493, which claims priority to provisional application Ser. No. 60/041,746 filed on Mar. 28, 1997 and provisional application Ser. No. 60/041,751 filed on Mar. 28, 1997.

This application is also a continuation-in-part of application Ser. No. 09/378,188 filed on Aug. 20, 1999, now abandoned, which is a continuation of application Ser. No. 08/850,840 filed on May 3, 1997 now U.S. Pat. No. 5,985,559, which is a continuation of application Ser. No. 08/847,009 filed Apr. 30, 1997, now U.S. Pat. No. 5,897,493, which claims priority to provisional application Ser. No. 60/041,746 filed on Mar. 28, 1997 and provisional application Ser. No. 60/041,751 filed on Mar. 28, 1997. All applications, except to the extent, if any, such incorporation would constitute new matter, are herein incorporated by reference in their entirety as if fully set forth herein.

FIELD OF THE INVENTION

This invention relates generally to the fields of genomics, bioinformatics, and drug development. More specifically, it relates to a database containing phenotypic and environmental data on groups of individuals for use in conjunction with gene sequences to identify disease-influencing genes and substances.

BACKGROUND OF THE INVENTION

The physical makeup of an individual is determined by his or her genes. Genes are comprised of DNA, which in turn consists of four nucleotides known as adenine(A), thymine(T), cytosine(C), and guanine(G). A particular series of nucleotides is known as a gene sequence. Each gene sequence codes for a protein. A defective or mutant gene sequence will not produce a working protein. The protein may not perform its purpose, the protein may carry out a different purpose than intended, too much protein may be made, too little protein may be made, or the protein may not be made at all. If the protein is essential to one or more functions of the body, disease will result.

Mutant gene sequences are either inherited or acquired. An inherited gene sequence is received from an individual's parents, while an acquired gene sequence results from an event in the individual's lifetime which changes the original gene sequence.

A classic example of an inherited mutant gene sequence is the sickle cell anemia gene. Sickle cell anemia is caused by the substitution of a single nucleotide (A to T) in the gene sequence of an individual. This single substitution results in the substitution of a single amino acid (glutamic acid to valine) in the resulting hemoglobin protein. The mutant hemoglobin protein produces crescent-shaped or sickled red blood cells in affected individuals, causing a decrease in the amount of oxygen that can be transported throughout the body. The lack of oxygen often results in kidney and heart failure, paralysis, and rheumatism, which are common symptoms of anemic individuals.

An example of an acquired mutant gene sequence is malignant melanoma, or skin cancer. Cancer results when normal cells in an individual's body either lose or gain certain functions, resulting in the unchecked growth of non-normal cells. These non-normal cells often form tumors and spread throughout the body, disrupting normal cell functions. A cancer such as malignant melanoma is caused when the original gene sequence in epidermal cells is changed or mutated by an environmental factor, such as UV radiation. Our cells contain repair mechanisms to fix such problems, but over time the gene sequences in epidermal cells acquire more and more mutations. Mutant proteins are then produced and cellular functions are disrupted. The individual then has skin cancer.

Although an individual's environment generally precipitates the development of cancer, many individuals have been found to have a predisposition to cancer. These individuals have gene sequences which are more likely to become mutated over a shorter period of time. Examples of such gene sequences are the BRCA1 and BRCA2 genes. Women carrying these gene sequences have a higher probability of developing breast and ovarian cancer than women who carry normal gene sequences. Thus, although the affected women's original gene sequences may not be mutated, they are more likely to become mutated due to their sequence or location on a chromosome.

Another factor that should be considered when discussing genetic diseases is whether they are monogenic or polygenic in nature. Sickle cell anemia and cystic fibrosis are examples of monogenic diseases, as they are caused by a single gene sequence. Most types of cancer, asthma, and diabetes are examples of polygenic diseases, as they are caused by a variety of genes. Polygenic diseases are also more likely to be influenced by an individual's environment. Not surprisingly, polygenic diseases are more difficult to diagnose and treat. Thus, the use of gene sequences in developing new drugs is dependent the monogenic or polygenic nature of genetic diseases.

Typically, individuals with diseases caused by inherited or acquired gene sequences have only their symptoms treated. Diabetes patients receive insulin shots to regulate their blood glucose levels, asthma patients use inhalers to allow normal respiratory functions, and cancer patients undergo chemotherapy and radiation therapy to remove cancerous tumors. Although these treatments are often able to alleviate or eliminate the symptoms, they are unable to remove the genetic bases of the diseases.

The genetic bases of many diseases were discovered in the 1940's by scientists such as Beadle and Tatum, who discovered that each gene codes for a protein. Researchers then rationalized that study of the relevant gene sequences could lead to effective drug treatments for genetic diseases. The technology was inadequate, however, until the 1970-80's, when Boyer and Cohen cloned DNA; Maxam, Gilbert, and Sanger figured out how to sequence DNA; and Mullis developed the polymerase chain reaction (PCR) technique to quickly amplify DNA sequences. Using genetics to find drug candidates soon became a practical option.

Before these techniques became available, the pharmaceutical industry's main method of finding new drugs was trial and error. Compounds that were found to mimic the body's natural compounds were tested in vitro, in animal models, and in clinical trials to see if they had a desirable effect in treating disease. This method is still used and has resulted in many well-known drugs, but it is expensive and time-consuming.

With the advent of improved genetic techniques, however, the pharmaceutical industry has begun concentrating on genetics as the most effective route to new drug discovery. Genomics companies can typically be classified into one of two groups.

The first group concentrates on gene sequencing in order to find both drug targets and drug candidates, usually in the form of proteins expressed by the gene sequences. Gene sequencing can either be in the form of random discovery, whereby genes are sequenced without regard to their functions, or in the form of targeted discovery, whereby a certain region of the genome which is tentatively associated with a disease is sequenced. In random discovery gene sequencing, potentially useful gene sequences are identified and assayed to determine if they can be used in drug development. One problem with random discovery gene sequencing is that the majority of the human genome contains introns, or gene sequences which do not code for proteins. One way to circumvent this problem is to sequence complementary DNA (cDNA) instead. cDNA is produced from messenger RNA (mRNA). mRNA, in turn, is transcribed from DNA and processed by certain enzymes which remove the introns. cDNA sequences thus code for un-interrupted proteins.

Targeted discovery gene sequencing is typically used with positional cloning, comparative gene expression, and functional cloning techniques, which are described in the next group.

The second group of genomics companies takes a more epidemiological approach by first researching families or groups of individuals having a similar disease, and then isolating the relevant genes. In this method, also known as positional cloning, blood samples are taken from the individuals and analyzed. The blood samples contain DNA, which is studied to identify certain regions of the genome which appear to be associated with the disease. Linking a region of the genome with a disease is known as linkage analysis or genetic linkage mapping. Once a region of the genome has been identified, it is sequenced via targeted discovery gene sequencing.

The second group of genomics companies also uses comparative gene expression to discover disease gene sequences. In comparative gene expression, mRNA from both healthy and diseased tissue is isolated. The mRNA is then used to produce cDNA, which is sequenced using targeted discovery gene sequencing. The gene sequences from both the healthy and diseased tissue are then compared. In addition, the identification of genes associated with disease can be made by studying the level of expression of genes in both the healthy and diseased tissue.

Another similar technique is functional cloning. Mutant or non-functional proteins in metabolic pathways are studied and identified. The proteins are sequenced using targeted discovery gene sequencing and these sequences are used to figure out the corresponding DNA gene sequences. Once the disease gene sequences have been identified, they can be used in drug development.

Genomics companies in the first group include Incyte Pharmaceuticals (Palo Alto, Calif.). Incyte uses random discovery gene sequencing to produce its LifeSeq™ and LifeSeq FL™ databases. These databases contain the sequences of hundreds of human genes. These databases are licensed to drug development companies who use the sequences to produce new drugs. Databases covering animals (ZooSeq™), plants (PhytoSeq™), and bacteria and fungi (PathoSeq™) are also available. Incyte has also developed bioinformatics software, which provides sequence analysis and data management for their databases. In addition, Incyte offers cDNA libraries of the gene sequences in their databases, which can be directly used in drug development.

Human Genome Sciences (Rockville, Md.) also concentrates on random discovery gene sequencing, and has sequenced an estimated 90% of the 100,000 genes in the human body. In addition to collaborating with drug development companies who use their gene sequences, HGS also has its own drug discovery and development division. A number of therapeutic proteins which appear effective in animal models are under study.

Hyseq, Inc. (Sunnyvale, Calif.) has its HyX Platform which is capable of processing and sequencing millions of blood and DNA samples. The HyX Platform includes DNA arrays of samples and probes, software-driven modules, industrial robots for screening DNA probes against DNA samples, and bioinformatic software to analyze the genetic information. Through the use of its HyX Platform, HyX believes it can carry out a variety of techniques, such as gene identification, gene expression level determination, gene interaction studies (for polygenic diseases), and genetic mapping.

Affymetrix, Inc. (Santa Clara, Calif.) has a GeneChip system consisting of disposable DNA probe arrays containing gene sequences on a chip, instruments to process the probe arrays, and software to analyze and manage the genetic information in the probe. The GeneChip system thus allows pharmaceutical and biotechnology companies to collect gene sequences and apply them to drug development.

On the other hand, the pharmaceutical industry has a number of genomics companies who first identify the genes which are likely to cause disease. After the genes are identified, they are sequenced and the gene sequences are used in drug development. Likewise, proteins implicated in disease can be identified and sequenced. The sequences can be used to discover the gene sequences, which are then used in drug development.

Myriad Genetics, Inc. (Salt Lake City, Utah) targets families with a history of genetic disease and collects their genetic material in order to identify hereditary disease-causing genes. Myriad is able to identify these genes by using positional cloning and protein interaction studies in combination with targeted discovery gene sequencing. Using these techniques, Myriad has been able to locate and identify eight disease-related gene sequences, including BRCA1 and BRCA2. These gene sequences are used by Myriad's pharmaceutical partners to develop new therapeutics.

Another genomics company which uses disease inheritance patterns together with gene sequencing is Sequana (La Jolla, Calif.). Sequana uses DNA collection of individuals with inherited diseases, genotyping and linkage analysis, physical mapping, and gene sequencing to find disease gene sequences. Sequana also has a proprietary bioinformatics system which includes data mining tools to automatically sort and organize much of its data. Like Myriad, Sequana has a number of alliances with drug development companies which license Sequana's gene sequences.

Millennium Pharmaceuticals, Inc. (Cambridge, Mass.) employs a broader range of technologies than Myriad and Sequana. In addition to positional cloning and targeted discovery gene sequencing, Millennium uses a number of other non-genetic techniques. cDNA libraries are prepared from mouse tissues and expressed using rapid expression of differential gene expression (RARE) technology. Different patterns of cDNA gene expression allow researchers to identify possible disease targets. Millennium also uses functional cloning techniques in order to identify the gene sequences of interesting proteins. Once a potentially useful gene sequence has been identified, biological assays and bioinformatics are used as additional analyses.

Genome Therapeutics Corporation (Waltham, Mass.) uses a combination of positional cloning techniques and targeted discovery gene sequencing, as well as random discovery gene sequencing to isolate and identify disease gene sequences. In addition, Genome Therapeutics also has pathogen programs, which sequence pathogen genomes. As many non-genetic human diseases result from infection by pathogens, Genome Therapeutics hopes to eliminate pathogens by developing drugs and vaccines using the pathogens' genomes.

Gene Logic, Inc. (Columbia, Md.) has an accelerated drug discovery system which emphasizes its restriction enzyme analysis of differentially expressed sequences (READS) technology. READS is similar in nature to comparative gene expression technology. In READS, normal and diseased tissues are compared in order to identify gene expression differences between the two. Genes which appear to be important in the diseased tissue are then analyzed. Restriction enzymes, which cut gene sequences at specific sites, are used to produce gene fragments. The gene fragments from the normal and diseased tissues will differ and can be compared. Gene Logic also has a Flow-thru Chip and genomic databases, which it licenses to drug development companies.

Progenitor (Columbus, Ohio) focuses on developmental biology. Growing cells and tissues are analyzed for their level of expression of certain genes. Study of growing cells and tissues may help discover treatments for diseases characterized by abnormal cell growth, such as cancer and osteoporosis. Progenitor also uses bioinformatics, gene mapping, and gene sequencing to isolate, identify, and sequence relevant gene sequences.

OncorMed, Inc. (Gaithersburg, Md.) has focused on the development of medical services using genetic information. Oncormed offers a number of tests for hereditary diseases such as breast and colon cancers and malignant melanoma. The medical services include measurements of replication error rates in tumors, molecular profiling of tumor suppresser genes, and gene sequencing. In addition, OncorMed has a genomics repository containing known cancer gene sequences.

U.S. Pat. No. 5,642,936 issued to Evans and assigned to OncorMed describes a method for identifying human hereditary disease patterns. According to the method, data is collected on individuals having a history of disease within their families. Factors related to each disease are given weights, and the weights for each individual are summed. If the sum is above a certain predetermined threshold value, the individual is deemed to have a hereditary risk for the disease. Records from a number of individuals having a hereditary risk for a disease are collected to form a database.

The methods used by the above companies all focus on the genetic aspect of hereditary disease. Gene sequencing and positional cloning represent the two approaches generally taken. However, very little emphasis is put on the environmental aspect of hereditary disease. An individual's environment is defined as his or her physical surroundings, geographical location, diet, lifestyle, etc. For many diseases which are genetic in origin, such as most cancers, an individual's environment plays a large role in determining whether or not the individual eventually develops the disease. Some individuals who have disease gene sequences develop diseases, while others who carry the exact same disease gene sequences do not. One purpose of collecting environmental data about individuals whose gene sequences are studied is to effectively rule out any non-genetic causes of disease. Another purpose is to discover if any individuals who are carrying disease gene sequences but who do not develop the disease have other compensatory gene sequences or factors which enable them to live disease-free.

To a certain extent, the second group of genomics companies do take into account a small amount of environmental data when they select individuals whose DNA they use for positional cloning analyses. The environmental data is usually in the form of a questionnaire or survey. However, the data is typically limited in scope to lifestyle questions, and is used only to help narrow the search for the specific disease gene in question.

In addition, most genomics companies are reluctant to share their data on individuals' with others, even those genomics companies which are studying the same gene sequences. As a result, each genomics company must gather its own data on individuals having a certain disease. For example, Sequana sent its own researcher to the island of Tristan de Cunha to study hereditary asthma, while Myriad is located in Salt Lake City to take advantage of the detailed family trees of the Mormons. For genomics companies searching for gene sequences, gathering environmental data on individuals is often an expensive, time-consuming, but necessary step. Genomics companies could potentially spend more of their time and money on actual disease gene isolation if they were able to obtain necessary environmental data from another source.

Another problem lies in the fact that when genomics companies do gather environmental data on the individuals whose gene sequences are studied, the environmental data represents only a small time frame of an individual's life. Few genomics companies continually collect data over a long period of time, and as a result, are not able to definitively rule out certain environmental factors which may affect disease progression. In addition, such data collections are unlikely to provide leads for factors which may prohibit the formation of disease.

OBJECTS AND ADVANTAGES OF THE INVENTION

Accordingly, it is a primary object of the present invention to provide a system and method for creating a database of information about individuals' environments over a period of time. Another object of the present invention is to provide a database containing information about individuals' environments which can be used with existing genomics databases. A further object of the present invention is to provide a method of using environmental information about an individual in conjunction with the individual's genotype to find disease-influencing genes or substances. It is another object of the present invention to use the disease-influencing genes or substances to find drug candidates or drug targets.

SUMMARY OF THE INVENTION

These objects and advantages are attained by a system and method for identifying a disease-influencing gene or protein. The method includes the step of selecting individuals having a risk factor for a certain disease. Each of the individuals is provided with a remotely programmable apparatus having a user interface for communicating queries to the individuals and for receiving responses. Each apparatus also includes a communication device, such as a modem, for communicating with a server through a communication network.

Queries relating to the individuals' environment are entered into the server and transmitted from the server to each individual's remote apparatus. After the individuals' have responded to the queries, the responses are sent back to the server and organized into a database. Data mining software is then used to distinguish the individuals into groups based on their environmental profiles. After a period of time, each group is then further divided into categories based on their disease progression. The genomes of all the individuals are then sequenced. Data mining techniques are used to find gene differences between the categories.

According to a second method of the invention, the individuals are first separated into groups according to their disease progressions. Data mining techniques are then used to further distinguish each group into categories based on the individuals' environmental profiles. The genomes of all the individuals are then sequenced, and data mining techniques are used to find gene differences between the categories.

A third embodiment of the invention provides a method for identifying disease-influencing substances. The method includes the step of selecting individuals having a risk factor for a certain disease. Each of the individuals is provided with a remotely programmable apparatus having a user interface for communicating queries to the individuals and for receiving responses. Each apparatus also includes a communication device, such as a modem, for communicating with a server through a communication network.

Queries relating to the individuals' environment are entered into the server and transmitted from the server to each individual's remote apparatus. After the individuals' have responded to the queries, the responses are sent back to the server and organized into a database. The genomes of all the individuals are then sequenced. The individuals are placed into groups based on their gene sequences. Each group is then separated into categories based on the individuals' disease progression. Data mining techniques are then used to find a disease-influencing substance between the categories of individuals by using the individuals environmental profiles.

The disease-influencing gene or substance isolated using these methods is preferably used to develop drug candidates or drug targets. Additionally, the isolation of the disease-influencing gene is preferably used to identify a corresponding disease-influencing protein, which can also be used to develop drug candidates or drug targets.

The present invention also provides a database and data processing system for storing and analyzing environmental information about individuals. The database and data processing system comprise a server for storing queries and the individuals' responses to the queries. The system also includes at least one remotely programmable apparatuses having a user interface for communicating queries to the individuals and for receiving the responses. Each apparatus also includes a communication device, such as a modem, for communicating with the server through a communication network.

The system also includes genotyping means in communication with the server for determining the individuals' gene sequences and a data mining software program accessible to the server for analyzing the individuals' gene sequences and environmental profiles. In particular, the data mining program includes: means for analyzing the responses in order to group the individuals having a similar behavioral and environmental profile, a similar disease progression, and a similar genotype; means for analyzing the responses in order to group the individuals having a similar disease progression; means for analyzing the responses in order to group the individuals having a similar genotype; and means for identifying a disease-influencing gene or substance. Alternatively, the database can be used with other genomics or bioinformatics databases and systems if the information is to be manipulated in different ways.

DESCRIPTION OF THE FIGURES

FIG. 6A is a listing of a sample script program according to the preferred embodiment of the invention.

FIG. 6B is a continuation of the listing of FIG. 6A.

FIG. 10 is a sample report displayed on a workstation of the system of FIG. 1.

FIG. 13 is a sample data table of the present invention.

FIG. 14 is a sample completed data table of the present invention.

DETAILED DESCRIPTION

The invention presents a system and method for creating a database containing environmental information about an individual to be used in conjunction with the individual's gene sequences to find new drug targets and drug candidates. In a preferred embodiment of the invention, remote monitors are used to collect the environmental information. It is to be understood that environmental information includes all non-genetic information about an individual, such as disease progression, diet, lifestyle, and geographical location.

Figure 1:
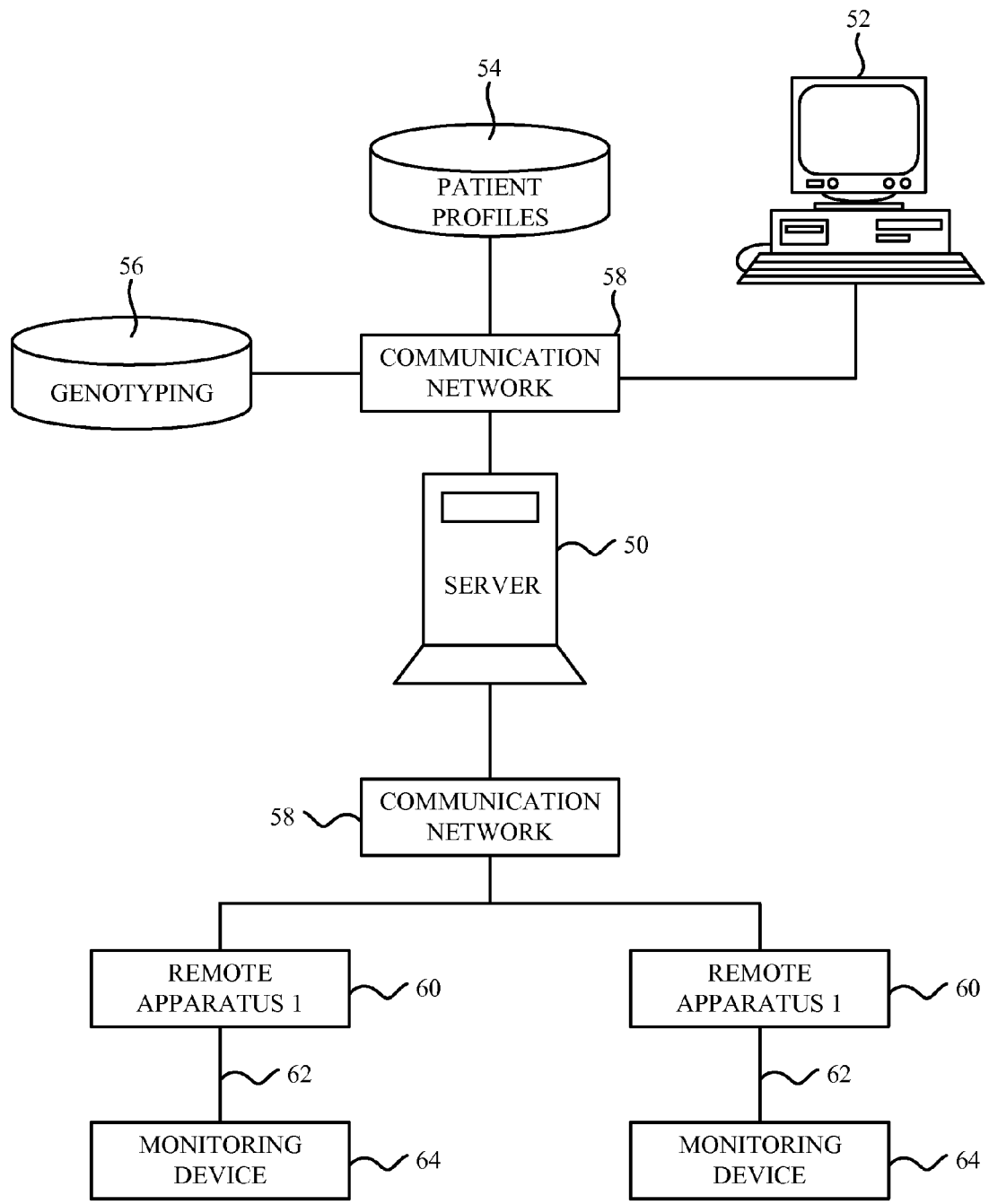
FIG. 1 is a block diagram of a networked system according to a preferred embodiment of the invention.

A preferred embodiment of the invention is illustrated in FIGS. 1-16. Referring to FIG. 1, a networked system includes a server 50 and a workstation 52 connected to server 50 through a communication network 58. Server 50 is also connected to a patient profile database 54 which stores environmental information about the individuals. Server 50 is further connected to a genotyping system 56 which is capable of sequencing individuals' genomes. Patient profile database 54 and genotyping system 56 are connected to server 50 through communication network 58.

Server 50 and patient profile database 54 are preferably world wide web servers. Server 50 and database 54 may comprise single stand-alone computers or multiple computers distributed throughout a network. Workstation 52 is preferably a personal computer, remote terminal, or web TV unit. Workstation 52 functions as a remote interface for entering in server 50 messages and queries to be communicated to the individuals.

Genotyping system 56 can be a laboratory capable of sequencing individuals' genomes, a gene sequencing chip such as the GeneChip by Affymetrix, or any other suitable genotyping system. Genotyping system 56 should be capable of transmitting information about the individuals' genomes to server 50. Communication network 58 connects workstation 52, patient profile database 54, and genotyping system 56 to server 50. Communication network 58 can be any suitable communication network, such as a telephone cable, the Internet, or cellular or wireless communication. Such communication networks are well known in the art.

The system also includes remotely programmable apparatuses 60 for monitoring individuals. Preferably, each remote apparatus 60 is used to monitor a respective one of the individuals. Alternatively, a multi-user apparatus may be used to monitor a plurality of individuals. Each remote apparatus is designed to interact with an individual in accordance with script programs received from server 50.

Each remote apparatus is in communication with server 50 through communication network 58, which is preferably the Internet. Alternatively, each remote apparatus may be placed in communication with the server via telephone cable, cellular communication, wireless communication, etc. For clarity of illustration, only two remote apparatuses are shown in FIG. 1. It is to be understood that the system may include any number of remote apparatuses for monitoring any number of individuals.

In the preferred embodiment, each individual to be monitored is also provided with a monitoring device 64. Monitoring device 64 is designed to produce measurements of a physiological condition of the individual, record the measurements, and transmit the measurements to the individual's remote apparatus 60 through a standard connection cable 62. Examples of suitable monitoring devices include blood glucose meters, respiratory flow meters, blood pressure cuffs, electronic weight scales, and pulse rate monitors. Such monitoring devices are well known in the art.

The specific type of monitoring device provided to each individual is dependent upon the individual's disease. For example, diabetes patients are provided with blood glucose meters for measuring blood glucose concentrations, asthma patients are provided with respiratory flow meters for measuring peak flow rates, obesity patients are provided with weight scales, etc.

Figure 2:
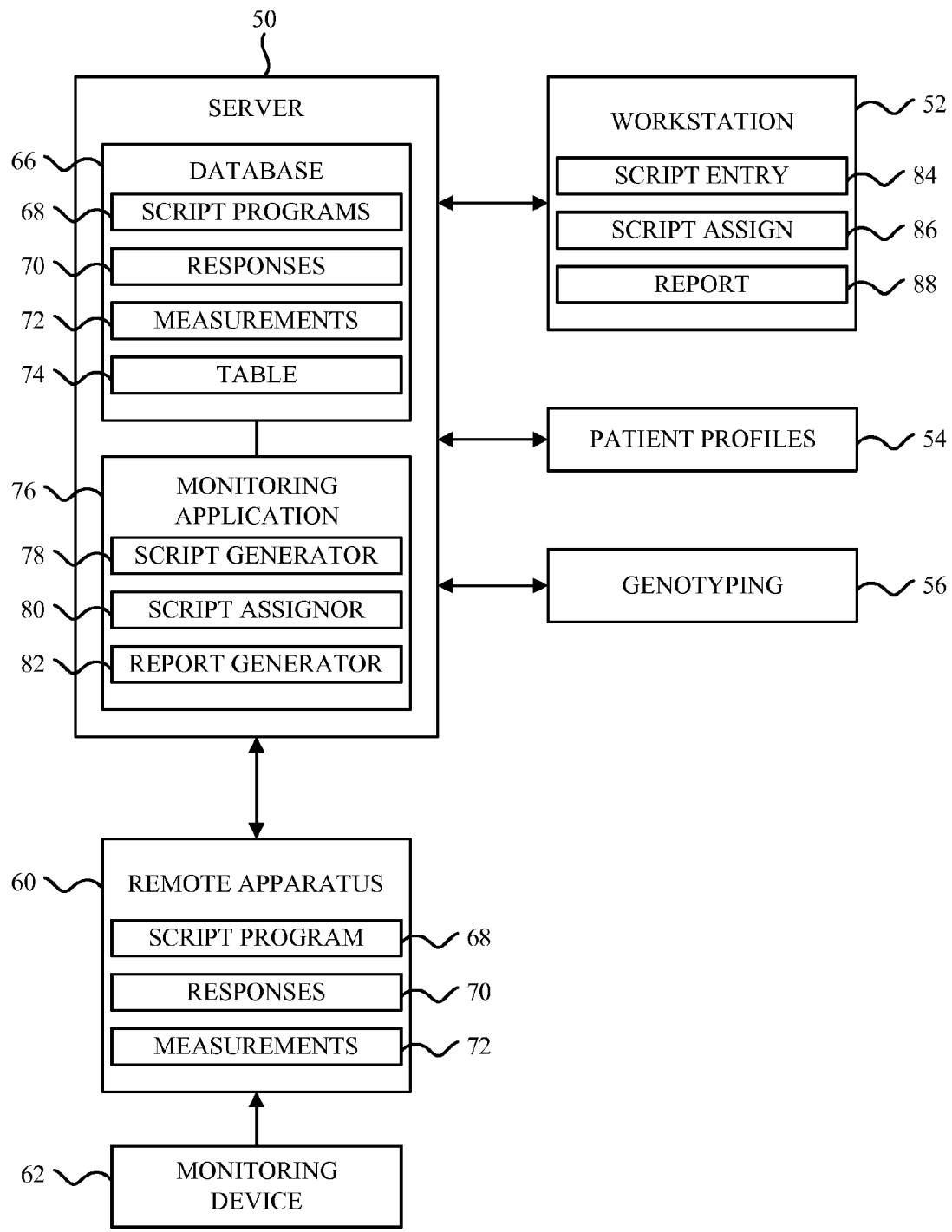
FIG. 2 is a block diagram illustrating the interaction of the components of the system of FIG. 1.

FIG. 2 shows server 50, workstation 52, and remote apparatus 60 in greater detail. Server 50 includes a database 66 for storing script programs 68. The script programs 68 are executed by each remote apparatus 60 to communicate queries and messages to an individual, receive responses 70 to the queries, collect monitoring device measurements 72, and transmit responses 70 and measurements 72 to server 50. Database 66 is designed to store the responses 70 and measurements 72. Database 66 further includes a look-up table 74. Table 74 contains a list of the individuals to be monitored, and for each individual, a unique individual identification code and a respective pointer to script program 68 assigned to the individual. Each remote apparatus 60 is designed to execute the assigned script program which it receives from server 50.

Figure 3:
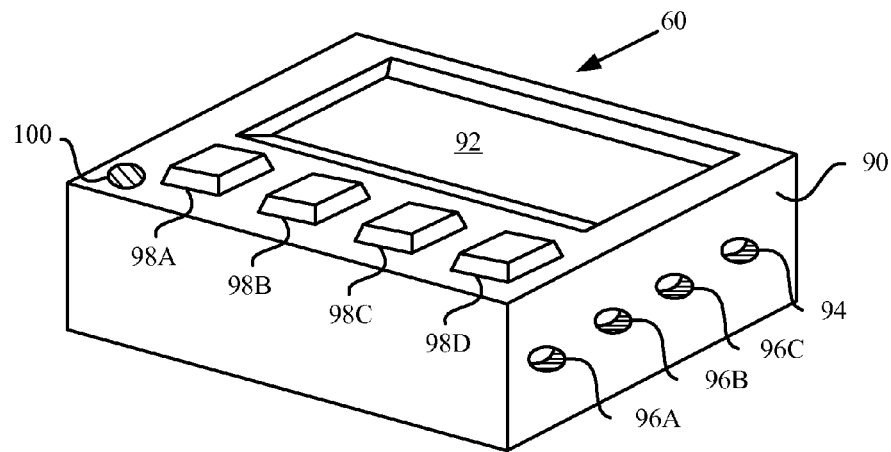
FIG. 3 is a perspective view of a remotely programmable apparatus of the system of FIG. 1.
Figure 4:
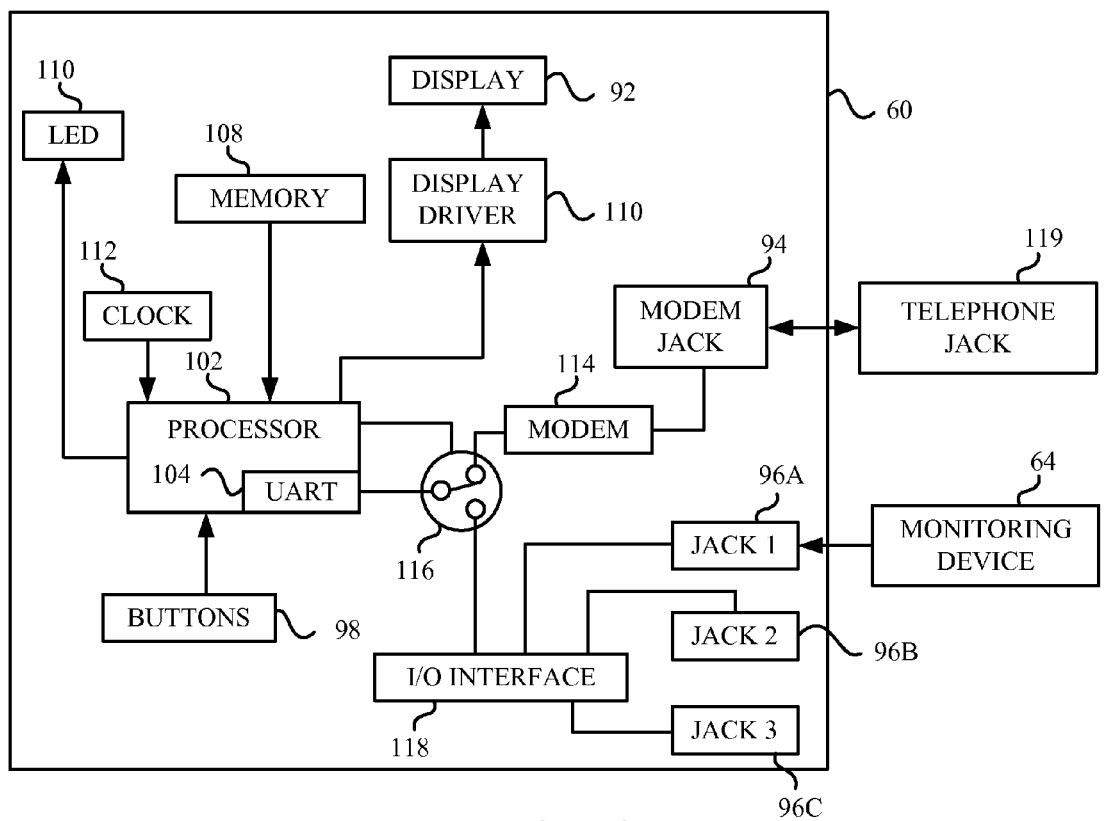
FIG. 4 is a block diagram illustrating the components of the apparatus of FIG. 3.

FIGS. 3-4 show the structure of remote apparatus 60 according to the preferred embodiment. Referring to FIG. 3, remote apparatus 60 includes a housing 90. Housing 90 is preferably sufficiently compact to enable the remote apparatus to be hand-held and carried by an individual. Remote apparatus 60 also includes a user interface for communicating queries to the individual and for receiving responses to the queries.

In the preferred embodiment, the user interface includes a display 92 and four user input buttons 98A, 98B, 98C, and 98D. Display 92 displays queries and prompts to the individual, and is preferably a liquid crystal display (LCD). The user input buttons 98A, 98B, 98C, and 98D are for entering responses to the queries and prompts. The user input buttons are preferably momentary contact push buttons. Although the user interface of the preferred embodiment includes a display and input buttons, it will be apparent to one skilled in the art of electronic devices that any suitable user interface may be used in remote apparatus 60. For example, the user input buttons may be replaced by switches, keys, a touch sensitive display screen, or any other data input device. Alternatively, the display and input buttons may be replaced by a speech synthesis/speech recognition interface.

Three monitoring device jacks 96A, 96B, and 96C are located on a surface of housing 90. Device jacks 96A, 96B, and 96C are for connecting remote apparatus 60 to a number of monitoring devices, such as blood glucose meters, respiratory flow meters, or blood pressure cuffs, through standard connection cables (not shown). Remote apparatus 60 also includes a modem jack 94 for connecting remote apparatus 60 to a telephone jack through a standard connection cord (not shown). Remote apparatus 60 further includes a visual indicator, such as a light emitting diode (LED) 100. LED 100 is for visually notifying the individual that he or she has unanswered queries stored in remote apparatus 60.

FIG. 4 is a schematic block diagram illustrating the components of remote apparatus 60 in greater detail. Remote apparatus 60 includes a microprocessor 102 and a memory 108 connected to microprocessor 102. Memory 108 is preferably a non-volatile memory, such as a serial EEPROM. Memory 108 stores script programs received from the server, measurements received from monitoring device 64, responses to queries, and the individual's unique identification code. Microprocessor 102 also includes built-in read-only memory (ROM) which stores firmware for controlling the operation of remote apparatus 60. The firmware includes a script interpreter used by microprocessor 102 to execute the script programs. The script interpreter interprets script commands which are executed by microprocessor 102. Specific techniques for interpreting and executing script programs in this manner are well known in the art.

Microprocessor 102 is preferably connected to memory 108 using a standard two-wire I$^2$C interface. Microprocessor 102 is also connected to user input buttons 98A, 98B, 98C, and 98D, LED 100, a clock 112, and a display driver 110. Clock 112 indicates the current date and time to microprocessor 102. For clarity of illustration, clock 112 is shown as a separate component, but is preferably built into microprocessor 102. Display driver 110 operates under the control of microprocessor 102 to display information on display 92. Microprocessor 102 is preferably a PIC 16C65 processor which includes a universal asynchronous receiver transmitter (UART) 104. UART 104 is for communicating with a modem 114 and a device interface 118. A CMOS switch 116 under the control of microprocessor 102 alternately connects modem 114 and interface 118 to UART 116.

Modem 114 is connected to a telephone jack 119 through modem jack 94. Modem 114 is for exchanging data with the server through the communication network. The data includes script programs which are received from the server as well as responses to queries, device measurements, script identification codes, and the individual's unique identification code which modem 114 transmits to server 50. Modem 114 is preferably a complete 28.8 K modem commercially available from Cermetek, although any suitable modem may be used.

Device interface 118 is connected to device jacks 96A, 96B, and 96C. Device interface 118 is for interfacing with a number of monitoring devices, such as blood glucose meters, respiratory flow meters, blood pressure cuffs, weight scales, or pulse rate monitors, through device jacks 96A, 96B, and 96C. Device interface 118 operates under the control of microprocessor 102 to collect measurements 72 from monitoring devices 64 and to output measurements 72 to microprocessor 102 for storage in memory 108. In the preferred embodiment, interface 118 is a standard RS232 interface. For simplicity of illustration, only one device interface 118 is shown in FIG. 4. However, in alternative embodiments, remote apparatus 60 may include multiple device interfaces to accommodate monitoring devices which have different connection standards.

Referring again to FIG. 2, server 50 includes a monitoring application 76. Monitoring application 76 is a controlling software application executed by server 50 to perform the various functions described below. Monitoring application 76 includes a script generator 78, a script assignor 80, and a report generator 82. Script generator 78 is designed to generate script programs 68 from script information entered through workstation 52. The script information is entered through a script entry screen 84. In the preferred embodiment, script entry screen 84 is implemented as a web page on the server 50. Workstation 52 includes a web browser for accessing the web page to enter the script information.

Figure 5:
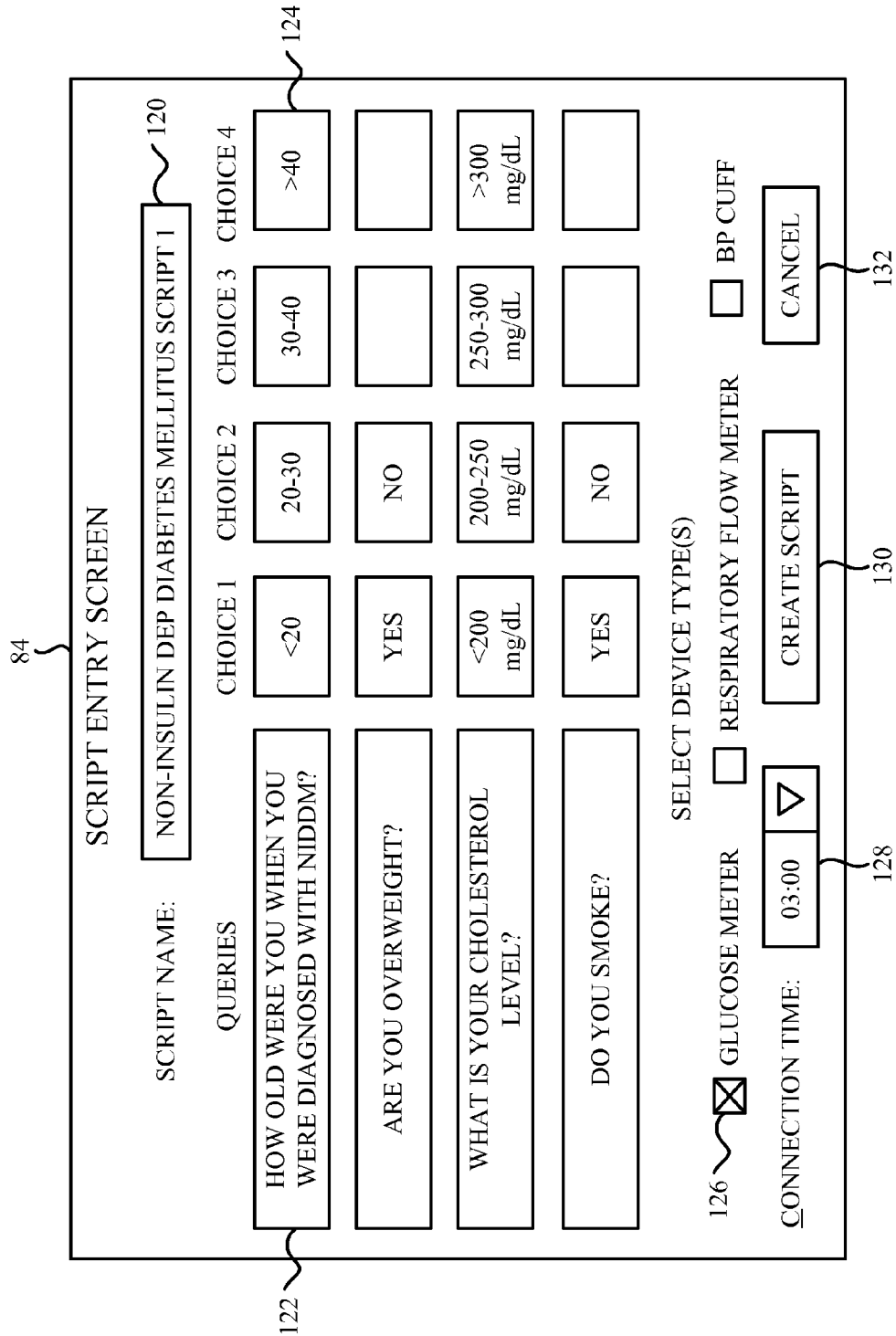
FIG. 5 is a script entry screen according to the preferred embodiment of the invention.

FIG. 5 illustrates script entry screen 84 as it appears on workstation 52. Script entry screen 84 includes a script name field 120 for specifying the name of script program to be generated. Screen 84 also includes entry fields 122 for entering a set of queries to be answered by an individual. Each entry field 122 has corresponding response choice fields 124 for entering response choices for the query. Screen 84 further includes check boxes 126 for selecting a desired monitoring device type from which to collect measurements, such as a blood glucose meter, respiratory flow meter, or blood pressure cuff.

Screen 84 additionally includes a connection time field 128 for specifying a prescribed connection time at which each remote apparatus executing the script program is to establish a subsequent communication link to the server. The connection time is preferably selected to be the time at which communication rates are the lowest, such as 3:00 AM. Screen 84 also includes a CREATE SCRIPT button 130 for instructing the script generator to generate a script program from the information entered in screen 84. Screen 84 further includes a CANCEL button 132 for canceling the information entered.

In the preferred embodiment, each script program created by the script generator 82 conforms to the standard file format used on UNIX systems. In the standard file format, each command is listed in the upper case and followed by a colon. Every line in the script program is terminated by a linefeed character {LF}, and only one command is placed on each line. The last character in the script program is a UNIX end of file character {EOF}. TABLE 1 shows an exemplary listing of script commands used in the preferred embodiment of the invention.

TABLE 1

SCRIPT COMMANDS

| Command | Description |
|---|---|
| CLS: {LF} | Clear the display. |
| ZAP: {LF} | Erase from memory the last set of query responses recorded. |
| LED: b{LF} | Turn the LED on or off, where b is a binary digit of 0 or 1. An argument of 1 turns on the LED, and an argument of 0 turns off the LED. |
| DISPLAY: {chars}{LF} | Display the text following the DISPLAY command. |
| INPUT: mmmm{LF} | Record a button press. The m's represent a button mask pattern for each of the four input buttons. Each m contains an "X" for disallowed buttons or an "O" for allowed buttons. For example, INPUT: OXOX{LF} allows the user to press either button #1 or #3. |
| WAIT: {LF} | Wait for any one button to be pressed, then continue executing the script program. |
| COLLECT: device{LF} | Collect measurements from the monitoring device specified in the COLLECT command. The user is preferably prompted to connect the specified monitoring device to the apparatus and press a button to continue. |
| NUMBER: aaaa{LF} | Assign a script identification code to the script program. The script identification code from the most recently executed NUMBER statement is subsequently transmitted to the server along with the query responses and device measurements. The script identification code identifies to the server which script program was most recently executed by the remote apparatus. |
| DELAY: t{LF} | Wait until time t specified in the DELAY command, usually the prescribed connection time. |
| CONNECT: {LF} | Perform a connection routine to establish a communication link to the server, transmit the patient identification code, query responses, device measurements, and script identification code to the server, and receive and store a new script program. When the server instructs the apparatus to disconnect, the script interpreter is restarted, allowing the new script program to execute. |

The script commands illustrated in TABLE 1 are representative of the preferred embodiment and are not intended to limit the scope of the invention. After consideration of the ensuing description, it will be apparent to one skilled in the art many other suitable scripting languages and sets of script commands may be used to implement the system and method of the invention.

Script generator 78 preferably stores a script program template which it uses to create each script program. To generate a script program, script generator 78 inserts into the template the script information entered in script entry screen 84. For example, FIGS. 6A-6B illustrate a sample script program created by the script generator from the script information shown in FIG. 5.

The script program includes display commands to display the queries and response choices entered in fields 122 and 124, respectively. The script program also includes input commands to receive responses to the queries. The script program further includes a collect command to collect device measurements from the monitoring device specified in check boxes 126. The script program also includes commands to establish a subsequent communication link to the server at the connection time specified in field 128. The steps included in the sample script program are also shown in the flow chart of FIGS. 12A-12B and will be discussed in the operation section below.

Referring again to FIG. 2, script assignor 80 is for assigning the script programs 68 to the individuals. The script programs are assigned in accordance with script assignment information entered through workstation 52. The script assignment information is entered through a script assignment screen 86, which is preferably implemented as a web page on server 50.

Figure 7:
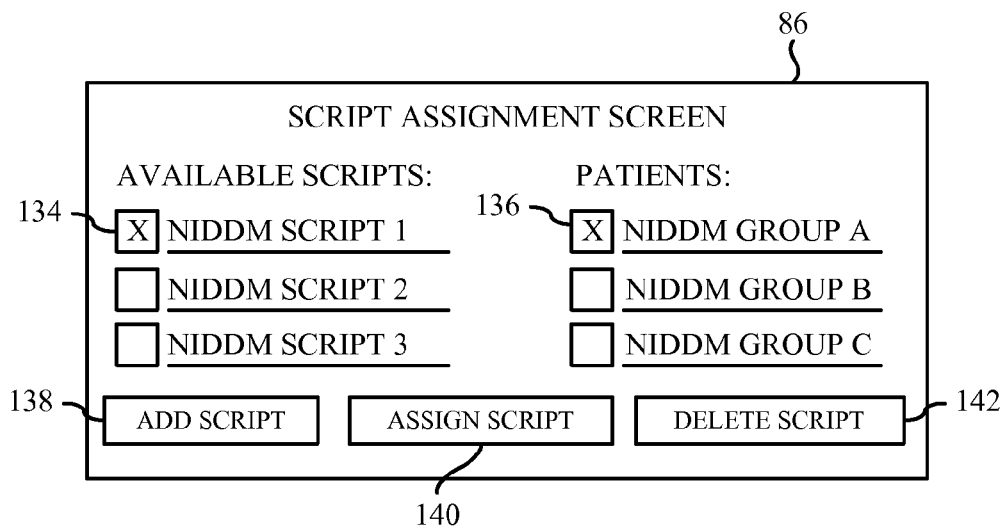
FIG. 7 is a script assignment screen according to the preferred embodiment of the invention.

FIG. 7 shows a sample script assignment screen 86 as it appears on the workstation. Screen 86 includes check boxes 134 for selecting the script program to be assigned and check boxes 136 for selecting the individuals to whom the script program is to be assigned. Screen 86 also includes an ASSIGN SCRIPT button 140 for entering the assignments. When button 140 is pressed, the script assignor creates and stores for each individual selected in check boxes 136 a respective pointer to the script program selected in check boxes 134. Each pointer is stored in the look-up table 74 of database 66. Screen 86 further includes an ADD SCRIPT button 138 for accessing the script entry screen and a DELETE SCRIPT button 142 for a deleting script program.

Referring again to FIG. 2, report generator 82 is designed to generate a report 88 from the responses 70 and device measurements 72 received in server 50. Report 88 is displayed on workstation 52. FIG. 10 shows a sample patient report 88 produced by report generator 82 for a selected individual. Report 88 includes a graph 146 of the device measurements received from the individual, as well as a listing of the query responses received from the individual. Specific techniques for writing a report generator program to display data in this manner are well known in the software art.

Figure 11:
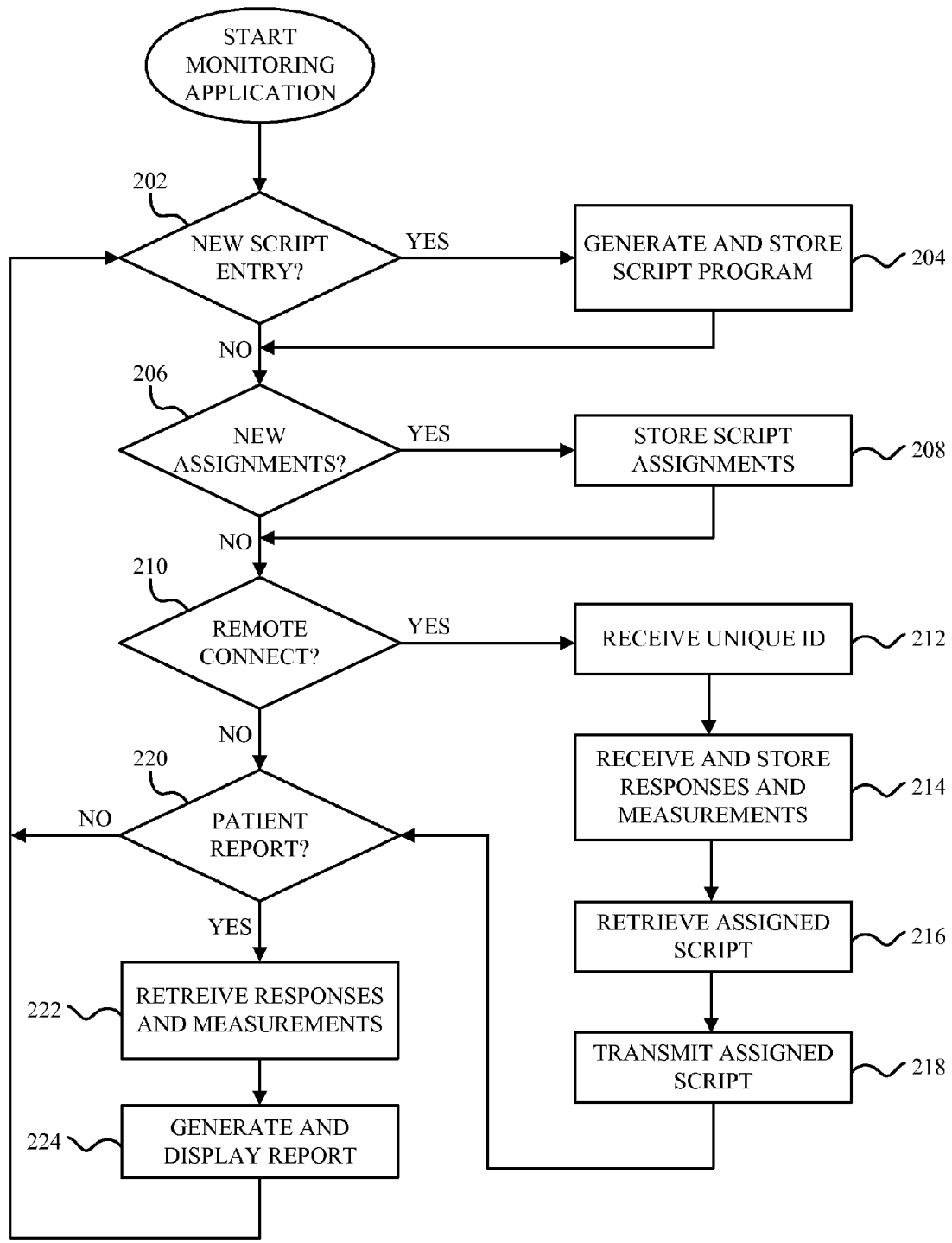
FIG. 11 is a flow chart illustrating the steps included in a monitoring application executed by the server of FIG. 1 according to the preferred embodiment of the invention.

The operation of the preferred embodiment is illustrated in FIGS. 1-12. FIG. 11 is a flow chart illustrating steps included in the monitoring application executed by server 50. In step 202, the server determines if new script information has been entered through script entry screen 84. If new script information has not been entered, the server proceeds to step 206. If new script information has been entered, the server proceeds to step 204.

As shown in FIG. 5, the script information includes a set of queries, and for each of the queries, corresponding responses choices. The script information also includes a selected monitoring device type from which to collect measurements. The script information further includes a prescribed connection time for each remote apparatus to establish a subsequent communication link to the server. The script information is generally entered in the server by a healthcare provider, such as the individuals' physician or case manager. Of course, any person desiring to communicate with the individual may also be granted access to the server to create and assign script programs. Further, it is to be understood that the system may include any number of workstations for entering script generation and script assignment information into the server.

In step 204, script generator 78 generates a script program from the information entered in screen 84. The script program is stored in database 66. Steps 202 and 204 are preferably repeated to generate multiple script programs, e.g. a script program for diabetes patients, a script program for asthma patients, etc. Each script program corresponds to a respective one of the sets of queries entered through script entry screen 84. Following step 204, the server proceeds to step 206.

In step 206, the server determines if new script assignment information has been entered through script assignment screen 86. If new script assignment information has not been entered, the server proceeds to step 210. If new script assignment information has been entered, the server proceeds to step 208. As shown in FIG. 7, script programs are assigned to each individual by selecting a script program through check boxes 134, selecting the individuals to whom selected the script program is to be assigned through check boxes 136, and pressing the ASSIGN SCRIPT button 140. When button 140 is pressed, script assignor 86 creates for each individual selected in check boxes 136 a respective pointer to the script program selected in check boxes 134. In step 208, each pointer is stored in look-up table 74 of database 66. Following step 208, the server proceeds to step 210.

In step 210, the server determines if any of the remote apparatuses are remotely connected to the server. Each individual to be monitored is preferably provided with his or her own remote apparatus which has the individual's unique identification code stored therein. Each individual is thus uniquely associated with a respective one of the remote apparatuses. If none of remote apparatuses are connected, the server proceeds to step 220.

If a remote apparatus is connected, the server receives from the apparatus the individual's unique identification code in step 212. In step 214, the server receives from the apparatus the query responses, device measurements, and script identification code recorded during execution of a previously assigned script program. The script identification code identifies to the server which script program was executed by the remote apparatus to record the query responses and device measurements. The responses, device measurements, and script identification code are stored in database 66.

In step 216, the server uses the individual's unique identification code to retrieve from look-up table 74 the pointer to the script program assigned to the individual. The server then retrieves the assigned script program from the database 66. In step 218, the server transmits the assigned script program to the individual's remote apparatus through the communication network 58. Following step 218, the server proceeds to step 220.

In step 220, the server determines if a report request has been received from workstation 52. If no report request has been received, the server returns to step 202. If a report request has been received for a selected individual, the server retrieves from database 66 the query responses and measurements last received from the individual, step 222. In step 224, the server generates and displays the report 88 on workstation 52.

As shown in FIG. 10, the report includes the query responses and device measurements last received from the individual. Following step 224, the server returns to step 202.

Figure 12:
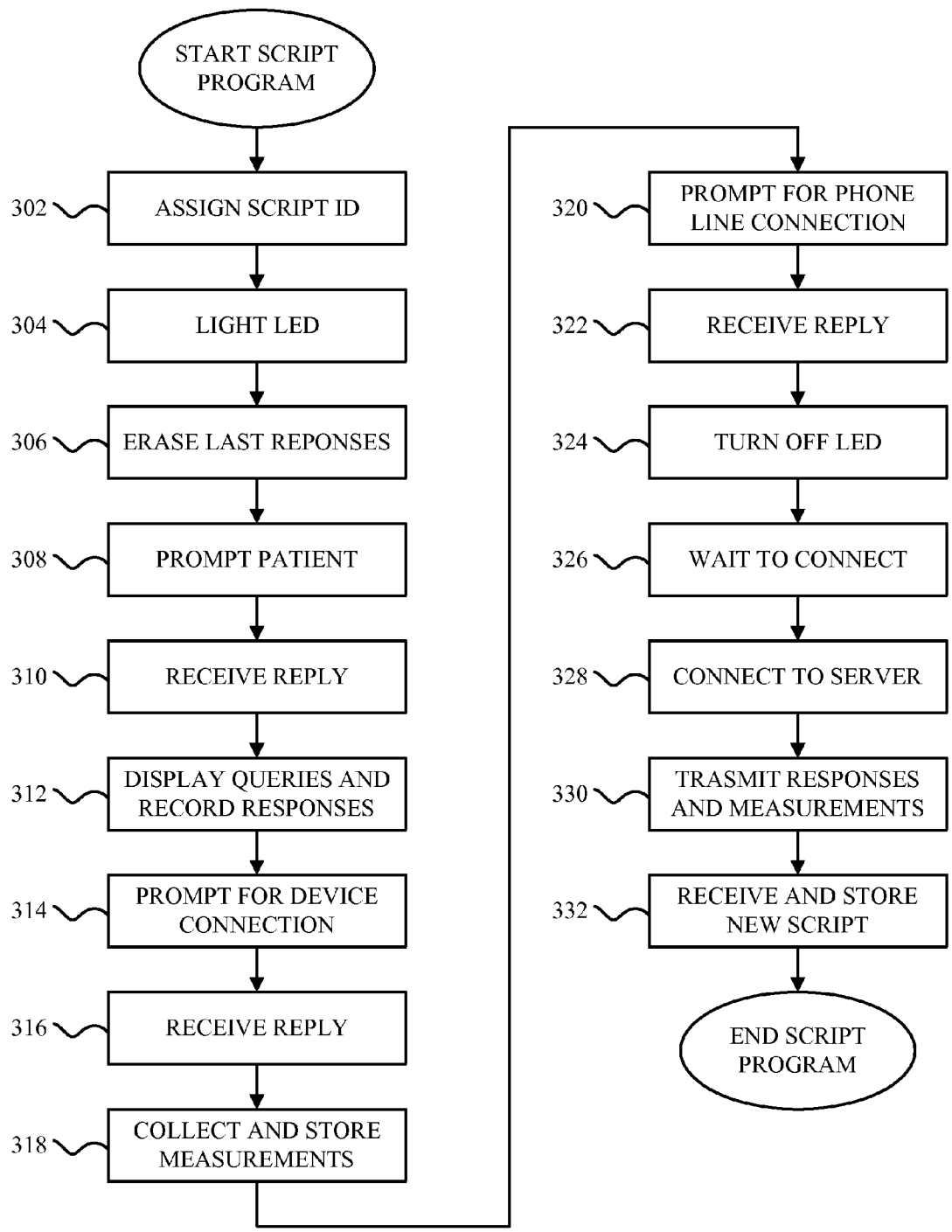
FIG. 12 is a flow chart illustrating the steps included in the script program of FIGS. 6A-6B.

FIG. 12 illustrates the steps included in a sample script program executed by the remote apparatus. Before the script program is received, the remote apparatus is initially programmed with the individual's unique identification code and the script interpreter used by microprocessor 102 to execute script programs. The initial programming may be achieved during manufacture or during an initial connection to the server. Following initial programming, the remote apparatus receives from the server the script program assigned to the individual associated with the apparatus. The script program is received by modem 114 through a first communication link to the server and stored in memory 108.

In step 302, microprocessor 102 assigns a script identification code to the script program and stores the script identification code in memory 108. The script identification code is subsequently transmitted to the server along with query responses and device measurements to identify to the server which script program was most recently executed by the remote apparatus. In step 304, microprocessor 102 lights LED 100 to notify the individual that he or she has unanswered queries stored in the remote apparatus. LED 100 preferably remains lit until the queries are answered by the individual. In step 306, microprocessor 102 erases from memory 108 the last set of query responses recorded.

In step 308, microprocessor 102 prompts the individual by displaying on display 92 "ANSWER QUERIES NOW? PRESS ANY BUTTON TO START". In step 310, microprocessor 102 waits until a reply to the prompt is received from the individual. When a reply is received, microprocessor 102 proceeds to step 312. In step 312, microprocessor 102 executes successive display and input commands to display the queries and response choices on display 92 and to receive responses to the queries.

Figure 8:
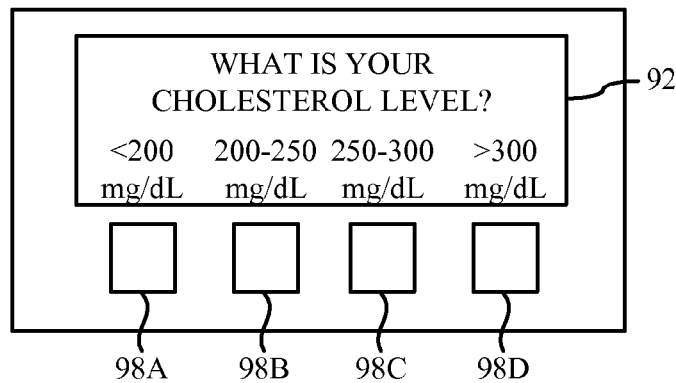
FIG. 8 is a sample query appearing on a display of the apparatus of FIG. 3.

FIG. 8 illustrate a sample query and its corresponding response choices as they appear on display 92. The response choices are preferably positioned on display 92 such that each response choice is located proximate a respective one of the user input buttons 98A, 98B, 98C, and 98D. In the preferred embodiment, each response choice is displayed immediately above a respective user input button. The individual presses the button corresponding to his or her response, and microprocessor 102 stores the response in memory 108.

Figure 9:
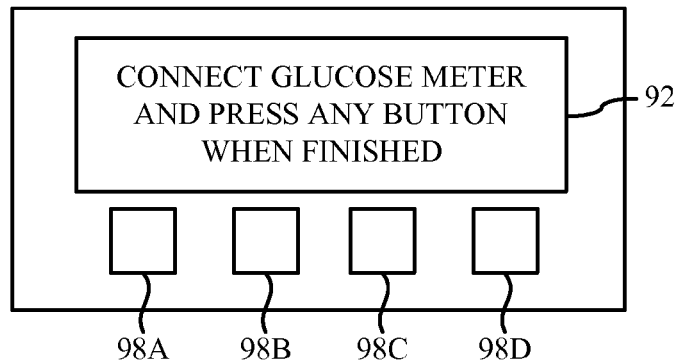
FIG. 9 is a sample prompt appearing on the display of the apparatus of FIG. 3.

In steps 314 to 318, microprocessor 102 executes commands to collect device measurements from a selected monitoring device specified in the script program. In step 314, microprocessor 102 prompts the individual to connect the selected device to one of the device jacks 96A, 96B, or 96C. A sample prompt is shown in FIG. 9. In step 316, microprocessor 102 waits until a reply to the prompt is received from the individual. When a reply is received, microprocessor 102 proceeds to step 318. Microprocessor 102 also connects UART 104 to device interface 118 through CMOS switch 116. In step 318, microprocessor 102 collects device measurements from the selected device through device interface 118. The device measurements are stored in memory 108.

In step 320, microprocessor 102 prompts the individual to connect remote apparatus 60 to telephone jack 119 so that the apparatus may connect to the server at the prescribed connection time. In step 322, microprocessor 102 waits until a reply to the prompt is received from the individual. When a reply is received, microprocessor 102 turns off LED 100 in step 324. In step 326, microprocessor 102 waits until it is time to connect to the server. Microprocessor 102 compares the connection time specified in the script program to the current time output by clock 112. When it is time to connect, microprocessor 102 connects UART 104 to modem 114 through CMOS switch 116.

In step 328, microprocessor 102 establishes a subsequent communication link between remote apparatus 60 and server 50 through modem 114 and communication network 58. If the connection fails for any reason, microprocessor 102 repeats step 328 to get a successful connection. In step 330, microprocessor 102 transmits the query responses, device measurements, script identification code, and the individual's unique identification code stored in memory 108 to the server. In step 332, microprocessor 102 receives through modem 114 a newly assigned script program from the server. The new script program is stored in memory 108 for subsequent execution by microprocessor 102. Following step 332, the script program ends.

After the individual's information has been collected via remote apparatus 60 and the script programs, the data is mined to distinguish patterns. Data mining programs are well known in the art and can be easily adapted to this system. In the preferred embodiment, the data mining program includes a data table 150, as shown in FIG. 13. Data table 150 is stored on the server and has an individual identification number field 151, name fields 152, value fields 154 corresponding to the name fields, and explanation fields 156 corresponding to the name fields and value fields. The data type is entered into name fields 152, the possible numerical values corresponding to the data type are entered into value fields 154, and brief explanations of the data types and corresponding values are entered into explanation fields 156.

The individuals' device measurements and responses to the queries are entered into data table 150 in the form of numerical values in value fields 154. The individual's identification number is entered into individual identification number field 151. An example of data table 150 in which the individuals' information has been entered is shown in FIG. 14. Once data table 150 contains all the necessary information, the data mining program then compares the information.

Figure 15:
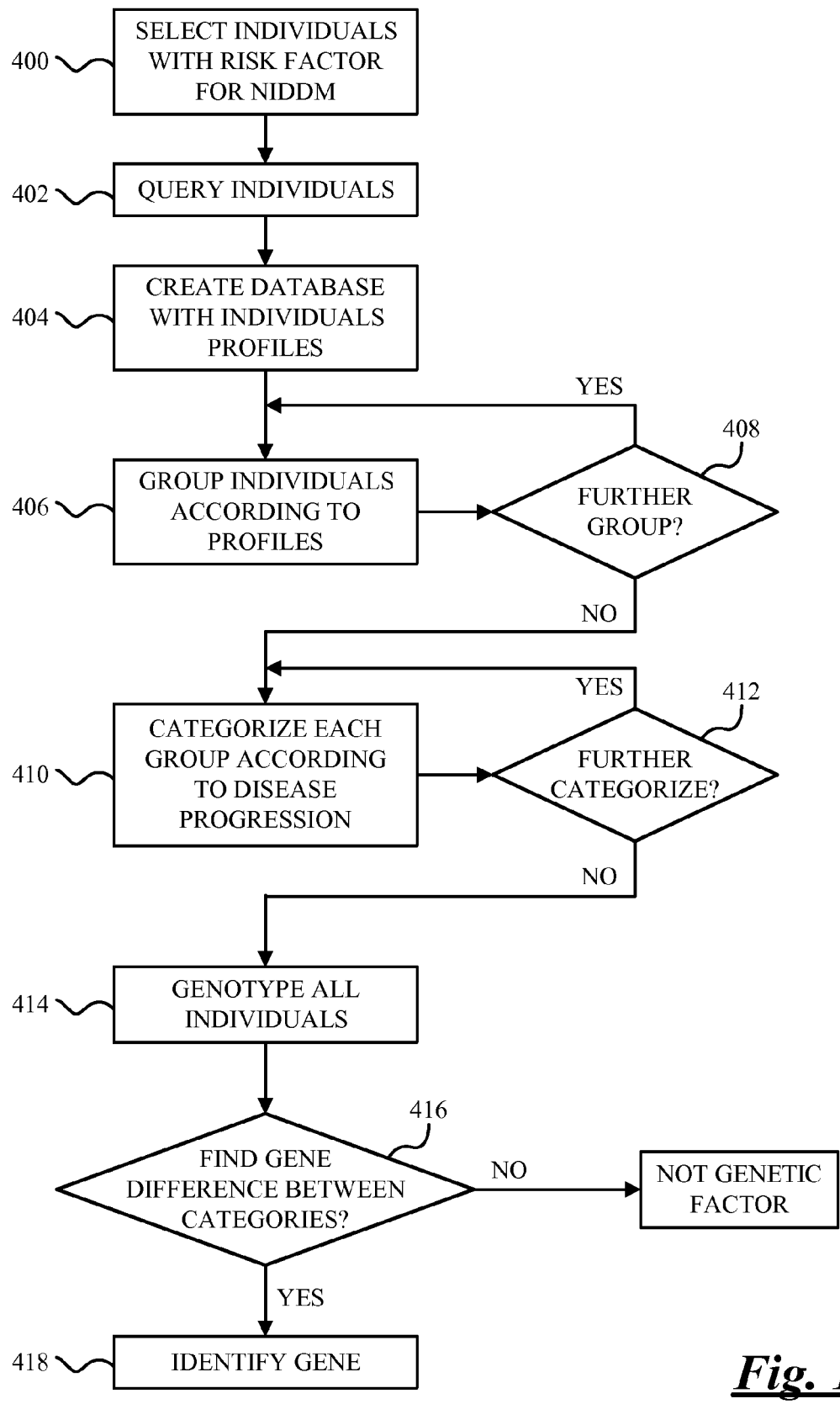
FIG. 15 is a flow chart illustrating a first method for identifying a gene according to the present invention.

FIG. 15 is a flowchart illustrating a first method of the present invention carried out by the server using the data mining techniques described above. In step 400, individuals having a risk factor for a disease are selected. In step 402, these individuals are queried about their behavior and environment using the script programs and remote apparatuses previously described. The responses to the queries and any device measurements are received and stored by the server. Collection of the responses and device measurements can occur over any period of time, thus allowing for more accurate data.

After the server receives the responses and measurements, a database comprising the individuals' behavioral and environmental profiles is created in step 404. In step 406, data mining techniques are used to group individuals having similar behavioral and environmental profiles. In step 408, the server determines if it is necessary to further group the individuals in order to produce smaller groups. Steps 406 and 408 can be repeated as often as necessary.

In step 410, each group of individuals is categorized using data mining techniques. The individuals are categorized according to their disease progressions. For example, a group of individuals can be categorized into those that have a severe disease phenotype, those that have a moderate disease phenotype, and those that have a mild disease phenotype. In step 412, the server determines if it is necessary to further categorize the individuals. Steps 410 and 412 can be repeated as often as necessary.

In step 414, the genomes of all the individuals are sequenced by genotyping system 56. The genotypes of all the individuals are transmitted to server 50. In step 416, data mining techniques are used to compare the genotypes of the individuals between the categories. For example, if those individuals who have a severe disease phenotype and are overweight have a certain gene sequence, while those individuals who have a mild disease phenotype and are overweight do not, it is likely the gene sequence is responsible for the severe disease phenotype. If a gene sequence is found, it is further identified in step 418. Methods of isolating and identifying gene sequences are well known in the field.

Figure 16:
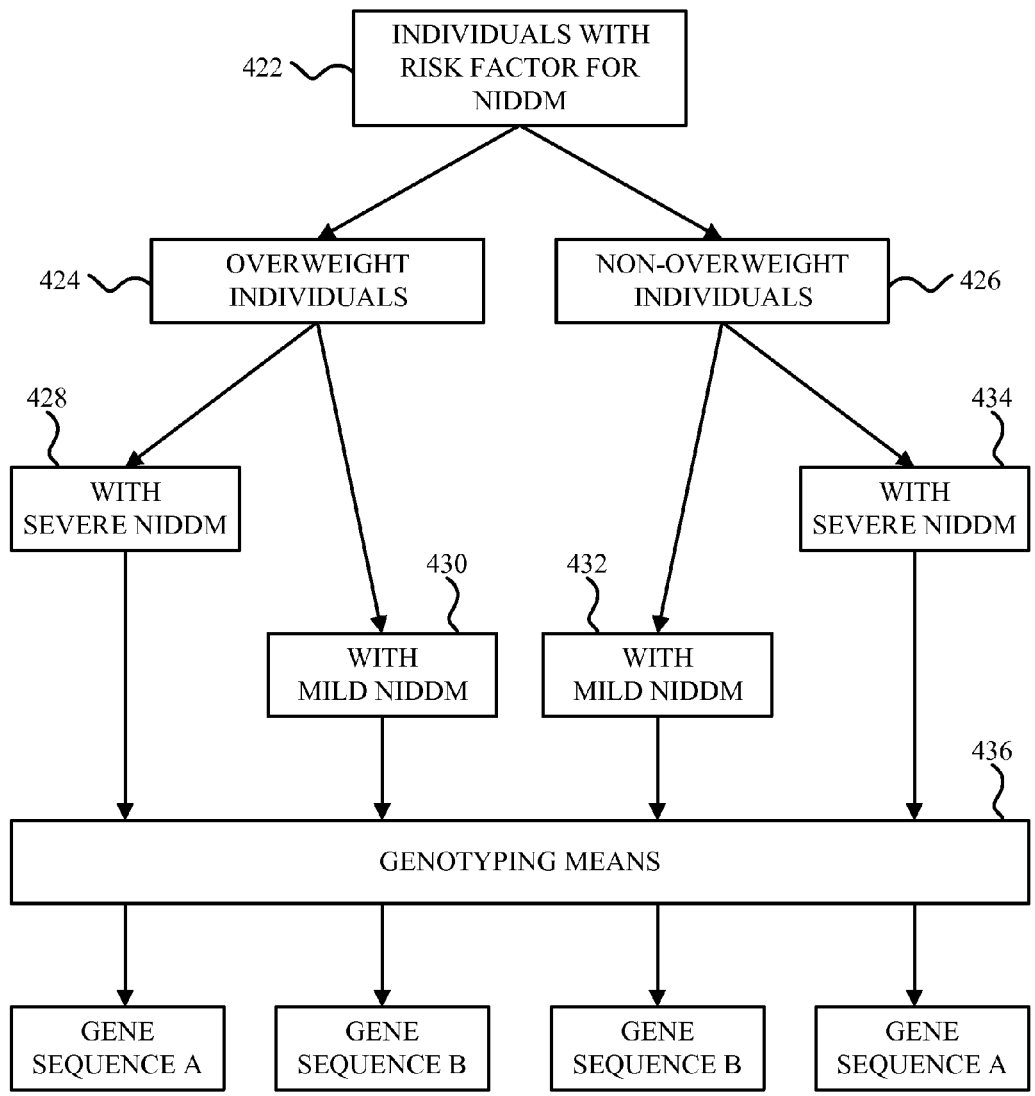
FIG. 16 is a block diagram illustrating the method of FIG. 15.

FIG. 16 is a block diagram illustrating an example of the first method of the present invention as described in FIG. 15. First individuals having a risk factor for a certain disease, such as non-insulin dependent diabetes mellitus (NIDDM), are selected, as indicated at block 422. Behavioral and environmental information from each individual is collected using the script programs and remote apparatuses. Using data mining techniques, the individuals are then grouped into overweight individuals 424 and non-overweight individuals 426. Using data mining techniques, the individuals are then categorized into overweight individuals having severe NIDDM 428, overweight individuals having mild NIDDM 430, non-overweight individuals having mild NIDDM 432, and non-overweight individuals having severe NIDDM 434.

The individuals' genotype information is then taken, as indicated at block 436, to determine the individuals' gene sequences. For example, overweight individuals with severe NIDDM have gene sequence A, overweight individuals with mild NIDDM have gene sequence B, non-overweight individuals with mild NIDDM have gene sequence B, and non-overweight individuals with severe NIDDM have gene sequence A. Data mining techniques are then used to analyze the information and come to a conclusion. In this example, data mining would conclude that the severe NIDDM phenotype is likely related to gene sequence A, not the individual's weight.

Figure 17:
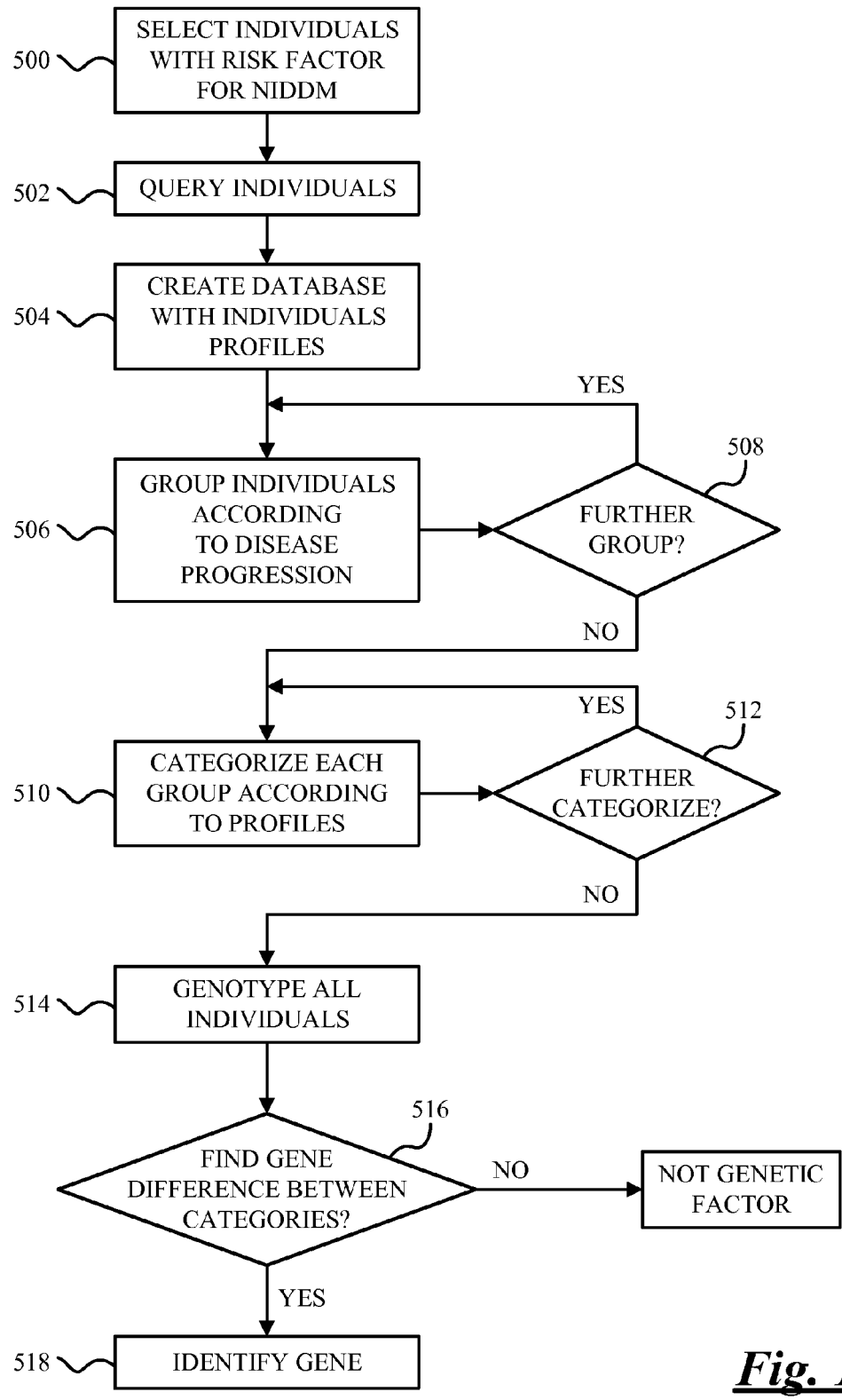
FIG. 17 is a flow chart illustrating a second method for identifying a gene according to the present invention.

FIG. 17 shows a flowchart illustrating a second method of the present invention carried out by the server using the data mining techniques described above. In step 500, individuals having a risk factor for a disease are selected. In step 502, these individuals are queried about their behavior and environment using the script programs and remote apparatuses previously described. The responses to the queries and any device measurements are received and stored by the server.

After the server receives the responses and measurements from the remote apparatuses, a database comprising the individuals' behavioral and environmental profiles is created in step 504. In step 506, data mining techniques are used to group together individuals having similar disease progressions. For example, a group of individuals can be grouped into those that have a severe disease phenotype, those that have a moderate disease phenotype, and those that have a mild disease phenotype. In step 508, the server determines if it is necessary to further group the individuals in order to produce smaller groups. Steps 506 and 508 can be repeated as often as necessary.

In step 510, each group of individuals created in steps 506 and 508 is categorized using data mining techniques according to the behavioral and environmental profiles of the individuals. In step 512, the server determines if it is necessary to further group the individuals in order to produce smaller groups. Steps 510 and 512 can be repeated as often as necessary.

In step 514, the genomes of all the individuals are sequenced by genotyping system 56. The genotypes of all the individuals are transmitted to the server. In step 516, data mining techniques are used to compare the genotypes of the individuals between the categories. For example, if those individuals who have a severe disease phenotype and are overweight have a certain gene sequence, while those individuals who have a mild disease and are also overweight phenotype do not, it is likely the gene sequence, not weight, is responsible for the severe disease phenotype. If a gene sequence is found, it is further identified in step 518. Specific techniques of isolating and identifying gene sequences are well known in the field.

Figure 18:
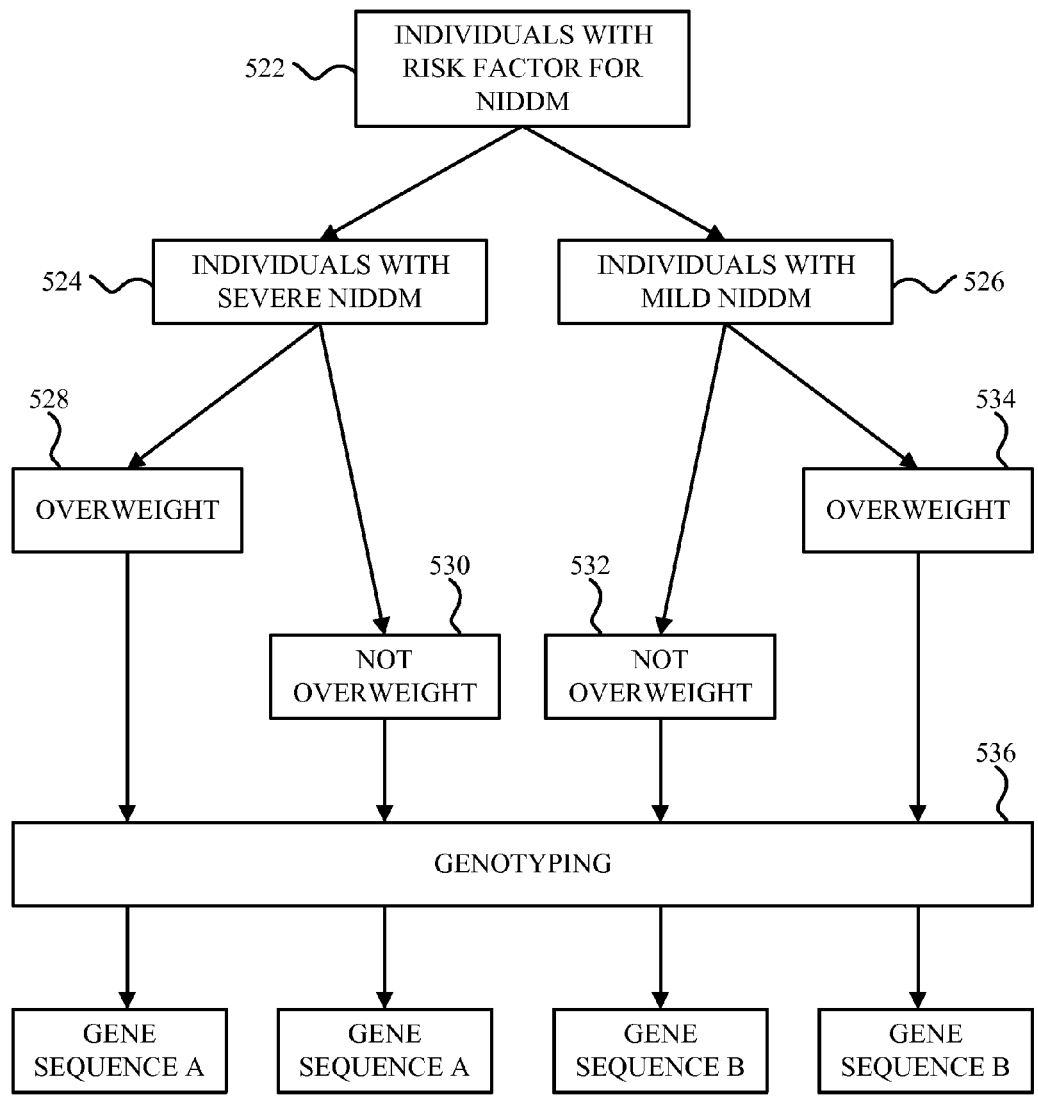
FIG. 18 is a block diagram illustrating the method of FIG. 17.

FIG. 18 is a block diagram illustrating an example of the second method of the present invention as described in FIG. 17. First individuals having a risk factor for a certain disease, such as NIDDM, are chosen, as indicated at block 522. Behavioral and environmental information from each individual is collected using the remote apparatuses and script programs. Using data mining techniques, the individuals are then grouped into those exhibiting severe NIDDM 524 and those exhibiting mild NIDDM 526. Using data mining techniques, the individuals are then categorized into overweight individuals having severe NIDDM 528, non-overweight individuals having severe NIDDM 530, non-overweight individuals having mild NIDDM 532, and overweight individuals having mild NIDDM 534.

The individuals' genotype information is then taken, as indicated at block 536, to determine the individuals' gene sequences. For example, individuals with severe NIDDM who are overweight have gene sequence A, individuals with severe NIDDM who are non-overweight have gene sequence A, individuals with mild NIDDM who are non-overweight have gene sequence B, and individuals with severe NIDDM who are overweight have gene sequence B. Data mining techniques are then used to analyze the information and come to a conclusion. In this example, data mining would conclude that the severe NIDDM phenotype is likely related to gene sequence A, not the individual's weight.

Figure 19:
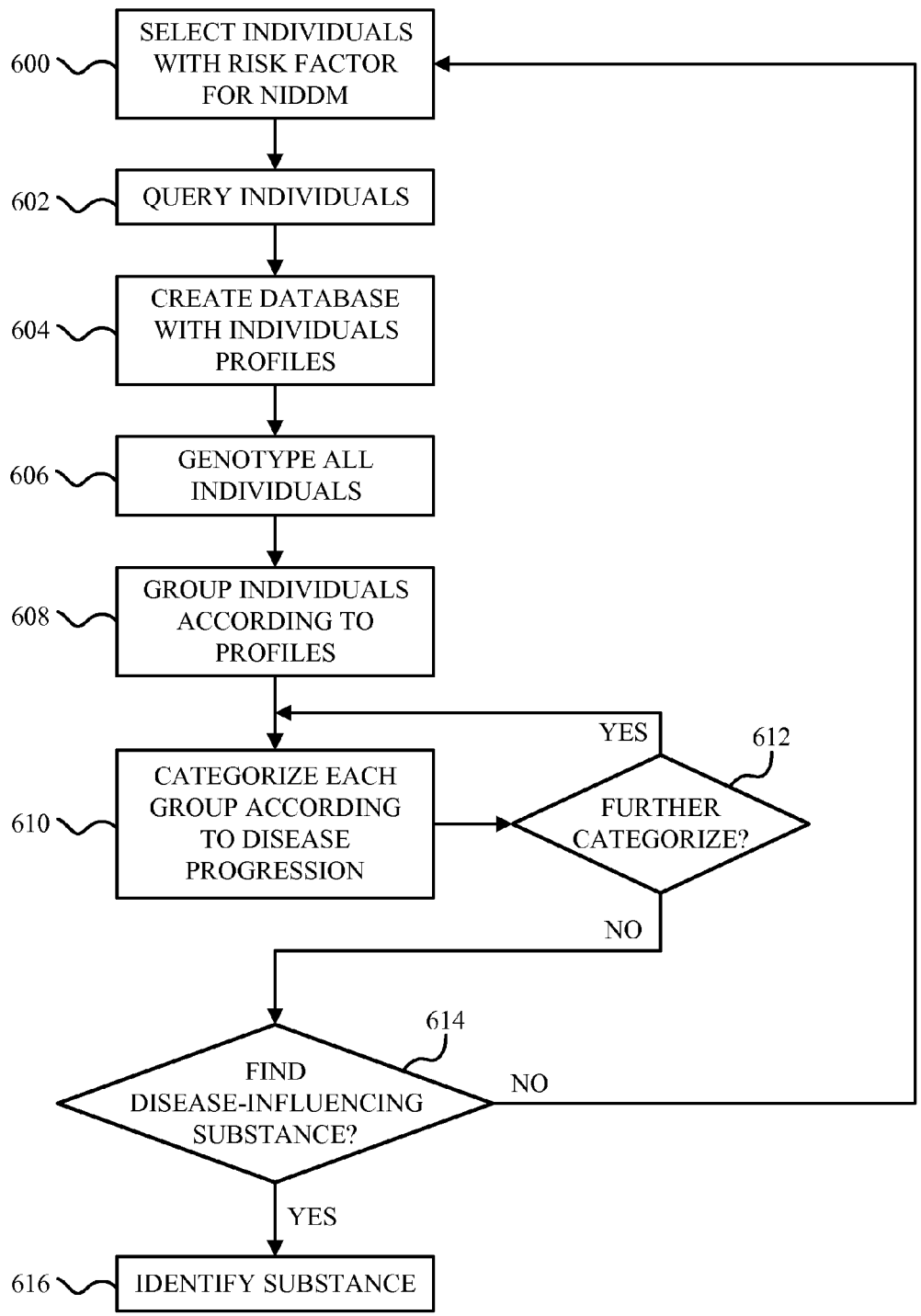
FIG. 19 is a flow chart illustrating a third method according to the present invention.

FIG. 19 shows a flowchart illustrating a preferred method carried out by server 50 to identify a disease-identifying substance. In step 600, individuals having a risk factor for a disease are selected. In step 602, these individuals are queried about their behavior and environment using the script programs and remote apparatuses previously described. The responses to the queries and any device measurements are received and stored by the server.

After the server receives the responses and measurements from the remote apparatuses, a database comprising the individuals' behavioral and environmental profiles is created in step 604. In step 606, the genomes of all the individuals are sequenced, and the genotypes of all the individuals are transmitted to the server. In step 608, individuals having the same or close genotypes are grouped together. In step 610, data mining techniques are used to categorize together individuals having similar disease progressions. In step 612, the server determines if it is necessary to further categorize the individuals in order to produce smaller groups. Steps 610 and 612 can be repeated as often as necessary.

In step 614, data mining techniques are used to find a disease-influencing substance between the categories of individuals by using the individuals behavioral and environmental profiles. For example, if those individuals who have a severe disease phenotype are overweight, while those individuals who have a mild disease phenotype are not, it is likely weight is responsible for the severe disease phenotype. If such a disease-influencing substance is found, it is identified in step 618. If no disease-influencing substance is found, the process is preferably repeated.

Figure 20:
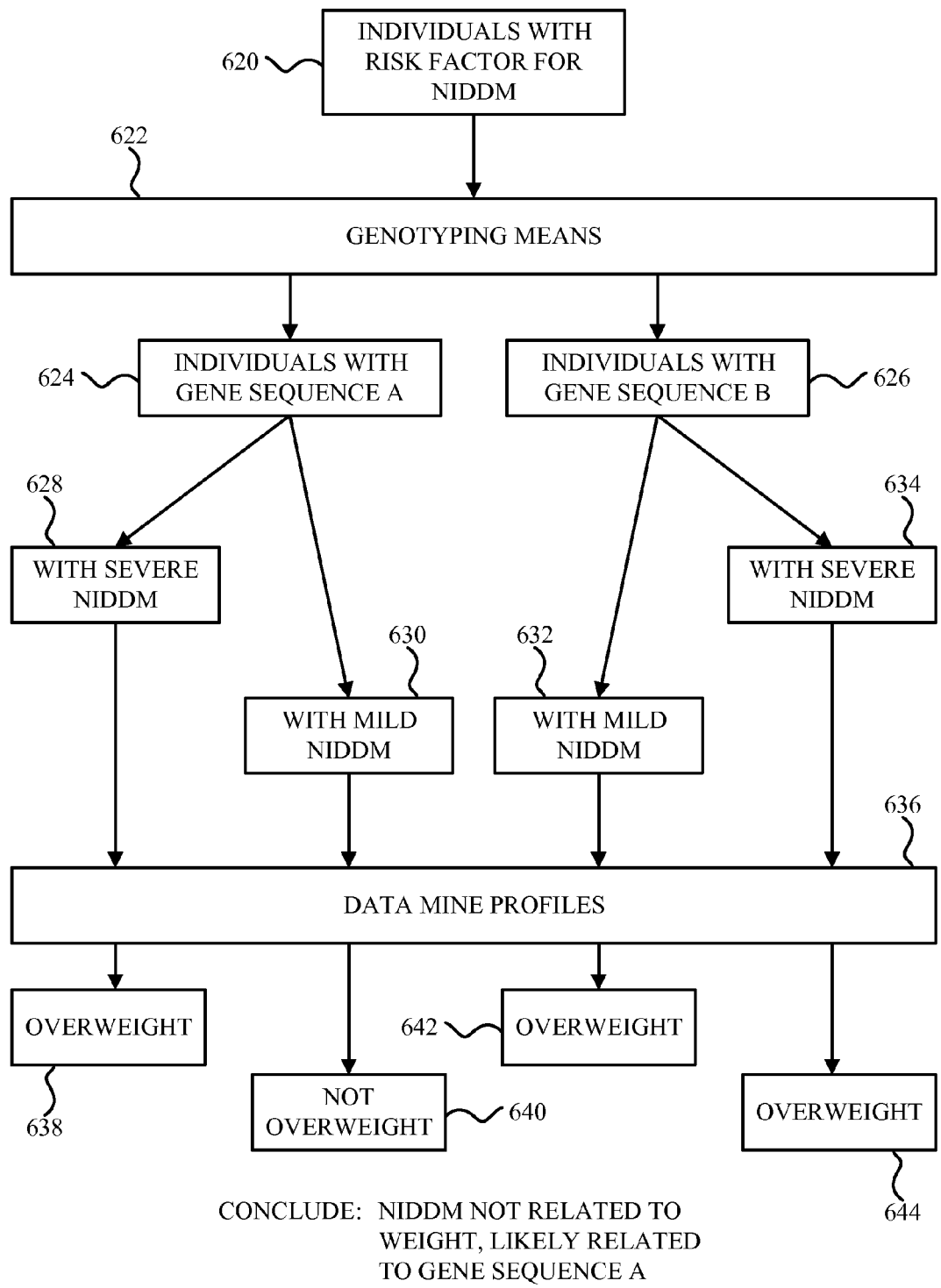
FIG. 20 is a block diagram illustrating the method of FIG. 19.

FIG. 20 is a block diagram illustrating an example of the method described in FIG. 19. First, individuals having a risk factor for a certain disease, such as NIDDM, are chosen, as indicated at block 620. Behavioral and environmental information from each individual is collected using the remote apparatuses and script programs. The individuals' genotype information is then taken, as indicated at block 622, to determine the individuals' gene sequences. The individuals are then grouped according to their gene sequences. For example, one group may have gene sequence A, as indicated at block 624, while another group may have gene sequence B, as indicated at block 626. Using data mining techniques, the individuals are then categorized into individuals with gene sequence A having severe NIDDM 628, individuals with gene sequence A having mild NIDDM 630, individuals with gene sequence B having mild NIDDM 632, and individuals with gene sequence B having severe NIDDM 634.

Data mining techniques are further used to analyze the categories of individuals and their behavioral and environmental profiles. For example, overweight individuals 638 with severe NIDDM have gene sequence A, non-overweight individuals 640 with mild NIDDM have gene sequence A, overweight individuals 642 with mild NIDDM have gene sequence B, and non-overweight individuals 644 with severe NIDDM have gene sequence B. Data mining techniques are then used to analyze the information and come to a conclusion. In this example, data mining would conclude that the severe NIDDM phenotype is likely related to gene sequence A, not the individual's weight.

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible. For example, the scripting language and script commands shown are representative of the preferred embodiment. It will be apparent to one skilled in the art that many other scripting languages and specific script commands may be used to implement the invention.

Moreover, the invention is not limited to the specific applications described. The system and method of the invention have many other applications. For example, pharmaceutical manufacturers may apply the system in clinical trials to analyze new drug data.

Therefore, the scope of the invention should be determined by the appended claims and their legal equivalents.

What is claimed is:

1. A method for generating groups of individuals useful in researching influence of a disease on said individuals, comprising:
    selecting individuals having a risk factor for a disease;
    providing to each individual a communications apparatus;
    transmitting a computer program containing queries and predefined response choices to said communications apparatus, wherein said computer program when executed causes said communications apparatus to present said queries and predefined response choices to each individual via a display of said communications apparatus and collect responses to said queries, including at least one of the predefined response choices presented on the display of the communications apparatus, from each individual via user input buttons of the communications apparatus;
    receiving said responses to the queries from the individuals through the communications apparatus, said responses communicating information about the individuals;
    storing the responses of each individual in a database;
    defining a plurality of groups by categorizing the individuals having similar profiles based on the responses, wherein categorizing the individuals into groups includes one or more phenotypic classifications;
    after defining said groups, receiving genotype information representative of individuals in each of said groups;
    comparing said genotype information between said groups; and
    generating a report for presentation on a display that represents a subset of said genotype information associated with each of said groups, wherein differences in said genotype information between said groups is expressed in terms of phenotypic classifications.

2. The method of claim 1, wherein the queries are inserted into said computer program with a script generator and assigned to an individual using a script assignor.

3. The method of claim 1, wherein categorizing the individuals into groups includes one of the phenotypic classifications from the set of behavioral, environmental, and disease progression.

4. The method of claim 1, wherein the communications apparatus is connectable with a monitoring device configured to acquire physiologic data.

5. The method of claim 4, wherein the monitoring device includes one of the set consisting of a blood glucose meter, a respiratory flow meter, a blood pressure cuff, a weight scale, and a pulse rate monitor.

6. A system for generating groups of individuals useful in researching influence of a disease on said individuals, comprising:
    a communications apparatus operable by an individual; and
    a communication network in signal communication with the communications apparatus and a server, a workstation configured to send scripted queries and predefined response choices, a genotyping system configured to provide genotype information representative of the individual, and a patient profile system configured to receive responses from the individual and genotype information analyses via the communications network and the server, wherein the server transmits a computer program containing the scripted queries and predefined response choices to the communications apparatus, the computer program when executed causes the communications apparatus to present the scripted queries and predefined response choices to the individual via a display of said communications apparatus and collect responses to the queries containing information about the individual and at least one of the predefined response choices presented on the display of said communications apparatus,
    whereby the genotype information is compared based upon groups formed by categorizing individuals having a risk factor for a disease using the responses to the scripted queries in the patient profile system to identify one or more individuals having similar profiles, wherein categorizing the individuals into groups includes one or more phenotypic classifications, and differences in said genotype information between said groups is expressed in terms of phenotypic classifications.

7. The system of claim 6, wherein the responses from the individual are used to categorize the individual into one or more groups and the one or more groups are compared with the genotype information of the individual to categorize said genotype information according to disease progression.

8. The system of claim 7, wherein the disease progression includes non-insulin dependent diabetes.

9. A system for identifying groups of individuals useful in researching influence of disease on said individuals, comprising:
    at least one communications apparatus in signal communication with a monitoring device configured to measure physiologic and environmental conditions, the communications apparatus and monitoring device being operable by at least one individual; and
    a communication network in signal communications with each communications apparatus and a server, a workstation configured to send scripted queries and predefined response choices, a genotyping system configured to provide genotype information representative of the at least one individual, and a patient profile system configured to receive responses and measurements from the at least one individual and genotype information analyses via the communications network and the server, wherein the server transmits a computer program containing the scripted queries and predefined response choices to the communications apparatus the computer program when executed causes the communications apparatus to present the scripted queries and predefined response choices to the individual via a display of the communications apparatus and collect responses to the scripted queries containing information about the individual and at least one of the predefined response choices presented on the display of said communications apparatus, whereby the genotype information representative of the at least one individual is compared based upon groups formed by categorizing individuals having a risk factor for a disease using the responses and measurements to the scripted queries in the patient profile system to identify one or more individuals having similar profiles, wherein categorizing the individuals into groups includes one or more phenotypic classifications, and differences in said genotype information between said groups is expressed in terms of phenotypic classifications.

10. The system of claim 9, wherein the monitoring device includes one of the set consisting of a blood glucose meter, a respiratory flow meter, a blood pressure cuff, a weight scale, and a pulse rate monitor.

11. The system of claim 9, wherein the responses and measurements from each individual are used to categorized each individual with one or more groups and the groups are compared with the genotype information representative of each individual to categorize the genotype information according to disease progression of each individual in the one or more groups based on the responses and measurements sent by each individual.

12. The system of claim 11, wherein the disease progression includes non-insulin dependent diabetes.

13. The system of claim 6, wherein categorizing the individuals into groups includes one of the phenotypic classifications from the set of behavioral, environmental, and disease progression.

14. The system of claim 9, wherein categorizing the individuals into groups includes one of the phenotypic classifications from the set of behavioral, environmental, and disease progression.

15. The method of claim 1, wherein the responses to the queries from the individuals communicate environmental information about the individuals.

16. The method of claim 15, wherein the environmental information comprises one or more of non-genetic information about an individual, information about disease progression, information about diet, information about lifestyle, and information about geographical location.

17. The method of claim 1, wherein the scripted queries contained in said computer program are related to one or both of behavior and environment of each individual.

* * * * *